(12) United States Patent
Jensen et al.

(10) Patent No.: US 9,965,862 B2
(45) Date of Patent: *May 8, 2018

(54) SYSTEM, METHOD AND COMPUTER ACCESSIBLE MEDIUM FOR PROVIDING REAL-TIME DIFFUSIONAL KURTOSIS IMAGING AND FOR FACILITATING ESTIMATION OF TENSORS AND TENSOR-DERIVED MEASURES IN DIFFUSIONAL KURTOSIS IMAGING

(71) Applicant: NEW YORK UNIVERSITY, New York, NY (US)

(72) Inventors: Jens Jensen, Scarsdale, NY (US); Joseph Helpern, Cornwall, NY (US); Ali Tabesh, New York, NY (US); Els Fieremans, New York, NY (US)

(73) Assignee: New York University, New York, NY (US)

( * ) Notice: Subject to any disclaimer, the term of this patent is extended or adjusted under 35 U.S.C. 154(b) by 867 days.

This patent is subject to a terminal disclaimer.

(21) Appl. No.: 14/462,215

(22) Filed: Aug. 18, 2014

(65) Prior Publication Data
US 2015/0055845 A1 Feb. 26, 2015

Related U.S. Application Data

(63) Continuation of application No. 13/022,488, filed on Feb. 7, 2011, now Pat. No. 8,811,706, which is a (Continued)

(51) Int. Cl.
*G06K 9/00* (2006.01)
*G06T 7/00* (2017.01)
(Continued)

(52) U.S. Cl.
CPC .......... *G06T 7/0081* (2013.01); *A61B 5/4088* (2013.01); *G01R 33/5608* (2013.01);
(Continued)

(58) Field of Classification Search
CPC ................. G06T 7/0012; G06T 7/0014; G06T 2207/10092; G06T 2207/30016;
(Continued)

(56) References Cited

U.S. PATENT DOCUMENTS 6,526,305 B1 * 2/2003 Mori ................ G01R 33/56341
128/920
6,614,226 B2 * 9/2003 Wedeen ................ A61B 5/055
324/307

(Continued)

OTHER PUBLICATIONS

Daniel C. Alexander, "Multiple-Fiber Reconstruction Algorithms for Diffusion MRI", Annals of the New York Academy of Sciences, vol. 1064, Dec. 2005, pp. 113-133.*

(Continued)

*Primary Examiner* — Eric Rush
(74) *Attorney, Agent, or Firm* — Andrews Kurth Kenyon LLP

(57) ABSTRACT

Exemplary method, system, and computer-accessible medium can be provided for determining a measure of diffusional kurtosis by receiving data relating to at least one diffusion weighted image, and determining a measure of a diffusional kurtosis as a function of the received data using a closed form solution procedure. In accordance with certain exemplary embodiments of the present disclosure, provided herein are computer-accessible medium, systems and methods for, e.g., imaging in an MRI system, and, more particularly for facilitating estimation of tensors and tensor-derived measures in diffusional kurtosis imaging (DKI). For example, DKI can facilitate a characterization of non-Gaussian diffusion of water molecules in biological tissues. The (Continued)

diffusion and kurtosis tensors parameterizing the DKI model can typically be estimated via unconstrained least squares (LS) methods. In the presence of noise, motion, and imaging artifacts, these methods can be prone to producing physically and/or biologically implausible tensor estimates. The exemplary embodiments of the present disclosure can address at least this deficiency by formulating an exemplary estimation problem, e.g., as linearly constrained linear LS, where the constraints can ensure acceptable tensor estimates.

30 Claims, 24 Drawing Sheets

Related U.S. Application Data continuation-in-part of application No. PCT/US2009/053223, filed on Aug. 7, 2009.

(60) Provisional application No. 61/087,111, filed on Aug. 7, 2008, provisional application No. 61/325,283, filed on Apr. 16, 2010.

(51) Int. Cl.
  A61B 5/00      (2006.01)
  G01R 33/56     (2006.01)
  G01R 33/563    (2006.01)
  G06T 7/11      (2017.01)

(52) U.S. Cl.
  CPC ...... *G01R 33/56341* (2013.01); *G06T 7/0012* (2013.01); *G06T 7/11* (2017.01); *A61B 2576/026* (2013.01); *G06T 2207/10088* (2013.01); *G06T 2207/10092* (2013.01); *G06T 2207/30016* (2013.01)

(58) Field of Classification Search
  CPC ........ G06T 2207/10088; A61B 5/0033; A61B 5/0042; A61B 5/4064; A61B 5/4082; A61B 5/4088; A61B 2576/026; G01R 33/5608; G01R 33/56341
  USPC .......................... 382/128, 131, 132, 168, 181
  See application file for complete search history.

(56) References Cited

U.S. PATENT DOCUMENTS

| | | | |
|---|---|---|---|
| 6,882,876 B2 | 4/2005 | Ulug | |
| 6,992,484 B2* | 1/2006 | Frank | G01R 33/56341 324/307 |
| 7,319,328 B1* | 1/2008 | Karmonik | G01R 33/56341 324/309 |
| 7,643,863 B2 | 1/2010 | Basser et al. | |
| 7,657,071 B2* | 2/2010 | Bartesaghi | G06T 7/0012 382/128 |
| 7,683,616 B2* | 3/2010 | Kabasawa | G01R 33/56341 324/309 |
| 8,076,937 B2* | 12/2011 | Holthuizen | G01R 33/5608 324/307 |
| 8,125,223 B2 | 2/2012 | K.N. et al. | |
| 2003/0009098 A1 | 1/2003 | Jack et al. | |
| 2006/0176488 A1* | 8/2006 | McGraw | G01R 33/56341 356/446 |
| 2006/0229856 A1* | 10/2006 | Burrus | G01R 33/56341 703/11 |
| 2008/0095463 A1 | 4/2008 | Abe | |
| 2008/0292194 A1 | 11/2008 | Schmidt et al. | |
| 2009/0099783 A1 | 4/2009 | Reisberg | |
| 2010/0080432 A1 | 4/2010 | Lilja et al. | |

OTHER PUBLICATIONS

Van J. Wedeen et al., Mapping Complex Tissue Architecture With Diffusion Spectrum Magnetic Resonance Imaging, Magnetic Resonance in Medicine, vol. 54, 2005, pp. 1377-1386.*

Yu-Chien Wu et al., "Hybrid diffusion imaging", Elsevier, NeuroImage, vol. 36, 2007, pp. 617-629.*

International Search Report dated Feb. 2, 2010 for International Application No. PCT/US2009/053223.

International Written Opinion dated Feb. 2, 2010 for International Application No. PCT/US2009/053223.

J. Jensen, et al. "Diffusional Kurtosis Imaging: The Quantification of NonGaussian Water Diffusion by Means of Magnetic Resonance . . . ," Magn. Res. in Med. 53;1432-1440 (2005).

Hui et al. "Towards Better MR Characterization of Neural Tissues Using Directional Diffusion Kurtosis Analysis" Neuroimage, 42;122-134 (2008).

Barmpoutis et al. "Regularized positive-definite fourth order tensor field estimation from DW-MR!," NeuroImage 45:S153-S162 (2009).

Basser et al. "MR diffusion tensor spectroscopy and imaging," Biophysical Journal 66:259-267 (1994).

Basser "Inferring microstructural features and the physiological state of tissues from diffusion-weighted images," NMR in Biomedicine 8:333-3442-3 (1995).

Sasser et al. "Microstructural and physiological features of tissues elucidated by quantitative-diffusion-tensor MRI," Journ. of Magnetic Resonance B 111:209-219 (1996).

Cheung et al. "Does diffusion kurtosis imaging lead to better neural tissue characterization? A rodent brain maturation study," NeuroImage 45:386-392 (2009).

Falangola et al. "Age-related non-Gaussian diffusion patterns in the prefrontal brain," Journal of Magnetic Resonance Imaging 28:1345-1350 (2008).

Jensen et al. "Quantifying non-Gaussian water diffusion by means of . . . ," In Proc. of the Intl. Soc. for Magn. Res. in Med. Annual Meeting, vol. 11, p. 2154, Toronto, CA 2003.

Koay et al. "Investigation of anomalous estimates of tensor-derived quantities in diffusion tensor imaging," Magnetic Resonance in Medicine 55:930-936 (2006).

Lazar et al. "Estimation of the orientation distribution function from diffusional kurtosis imaging," Magnetic Resonance in Medicine 60:774-781 (2008).

Liu et al. "Characterizing non-Gaussian diffusion by using generalized diffusion tensors," Magnetic Resonance in Medicine 51:924-937 (2004).

Lu et al. "Three-dimensional characterization of non-gaussian water diffusion in humans using diffusion kurtosis imaging," NMR in Biomedicine 19:236-247 (2006).

Raab et al. "Diffusional kurtosis imaging of cerebral gliomas—analysis of microstructural differences," Radiology, in press (2010).

Song et al. "Dysmyelination revealed through MRI as increased radial (but unchanged axial) diffusion of water," NeuroImage 17(3):1429-1436 (2002).

Wang et al. "A Constrained variational principle for direct estimation and smoothing of the diffusion tensor . . . ," IEEE Transactions on Medical Imaging 23:930-939 (2004).

Tournier, et al. "Direct Estimation of the fiber Orientation Density Function from Diffusion-Weighted MRI data using Spherical Deconvolution." NeuroImage. 23 (2004): 1176-1185.

Jensen, et al. "Diffusional Kurtosis Imaging: The Quantification of Non-Gaussian Water Diffusion . . . Imaging." Magnetic Resonance in Medicine. 53. (2005):1432-1440.

Hui, et al. "Towards better MR Characterization of Neural Tissues using Directional Diffusion Kurtosis Analysis." NeuroImage. 42. (2008): 122-134.

Behrens, et al. "Characteriziation and Propagation of Uncertainty in Diffusion-Weighted MR Imaging." Magnetic Resonance in Medicine. 50. (2003): 1077-1088.

Lu, et al. "Characterization of Non-Gaussian Water Diffusion in Humans using Diffusion Kurtosis Imaging." Proc. Intl. Soc. Mag. Reson. Med.. 13. (2005): 581.

(56) References Cited

OTHER PUBLICATIONS

Counsell, et al. "Axial and Radial Diffusivity in Preterm Infants Who Have . . . Magnetic Resonance Imaging at Term-Equivalent Age." Pediatrics. 117. (2006): 376-386.
Jondeau, et al. "Conditional Volatility, Skewness, and Kurtosis: Existence and Persistence." Banque de France Working papers. (2000): 1-49.
Jian, et al. "A Novel Tensor Distribution model for the Diffusion-Weighted MR Signal." NeuroImage. 37. (2007): 164-167.
DeCarlo, Lawrence. "On the Meaning and use of Kurtosis." Psychological Methods. 2.3 (1997): 292-307.

* cited by examiner

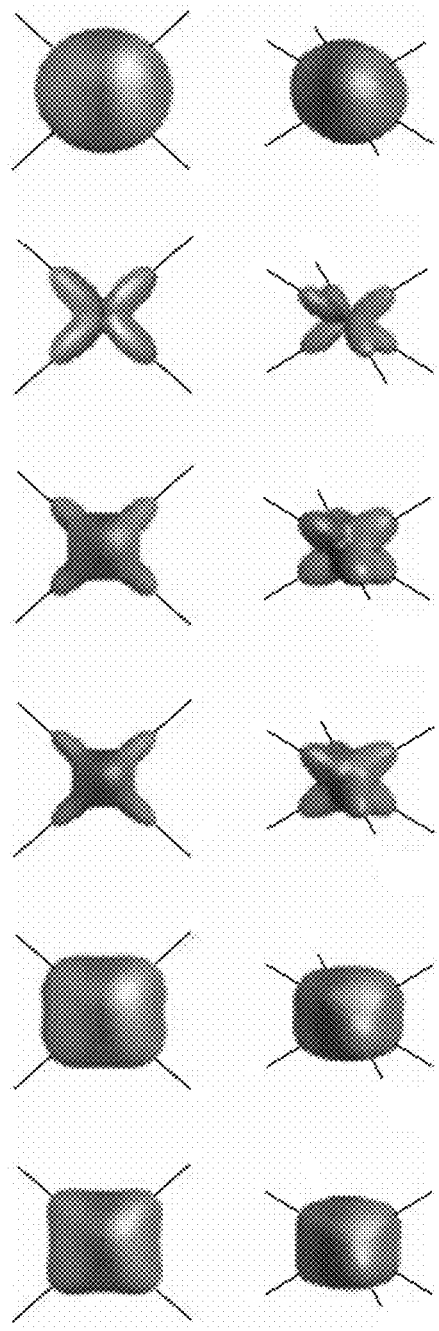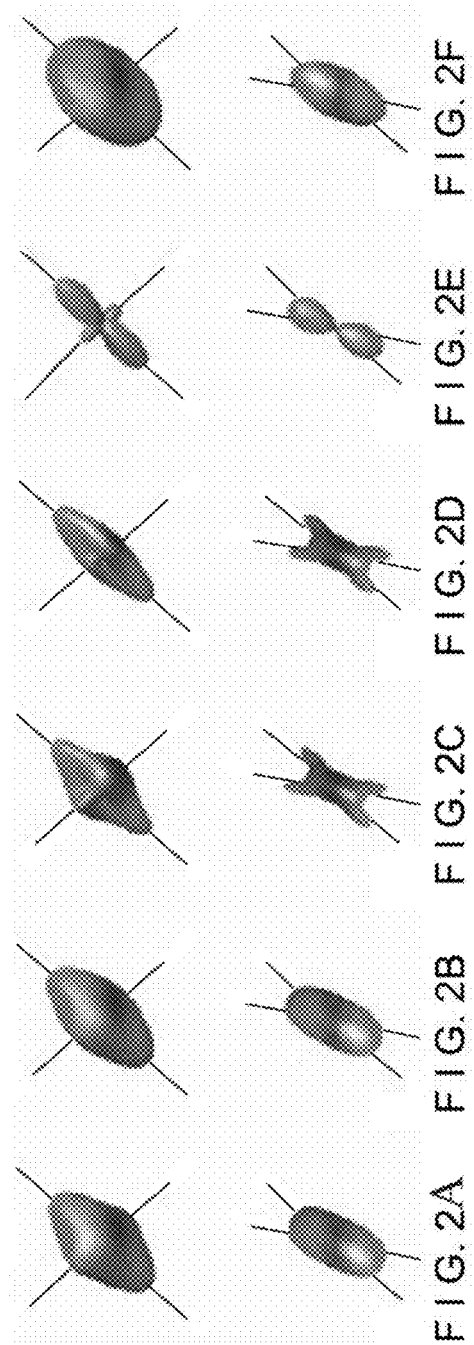

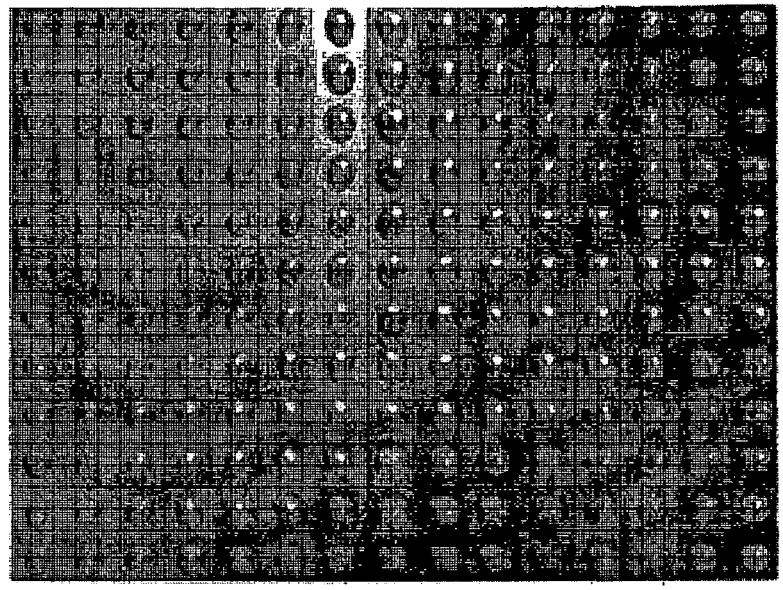
F I G. 5A
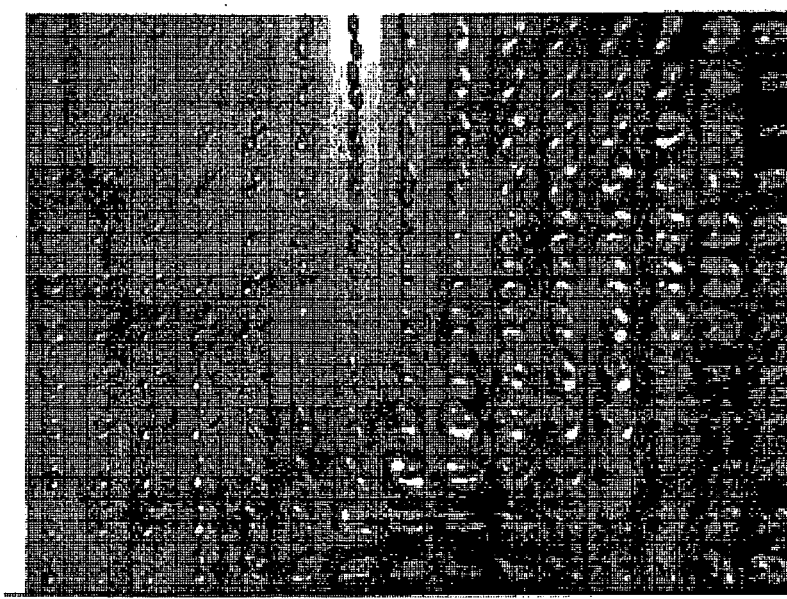
F I G. 5B

F I G. 5C
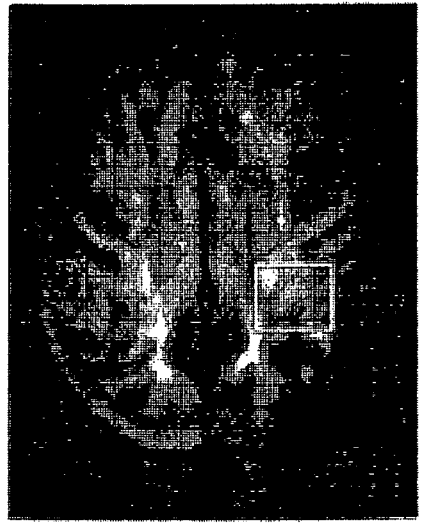
F I G. 5D
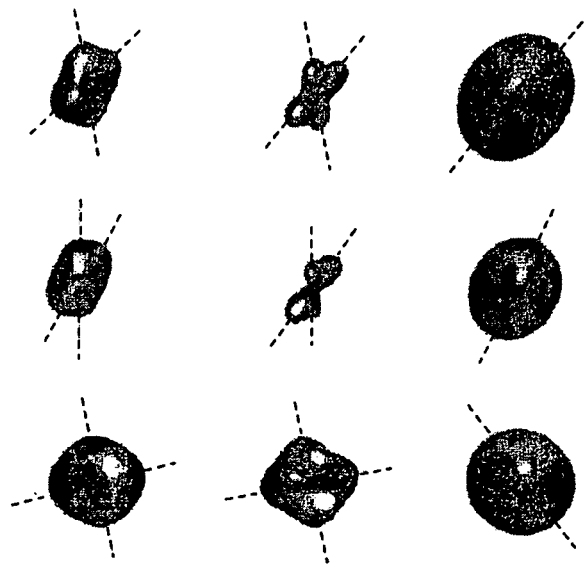

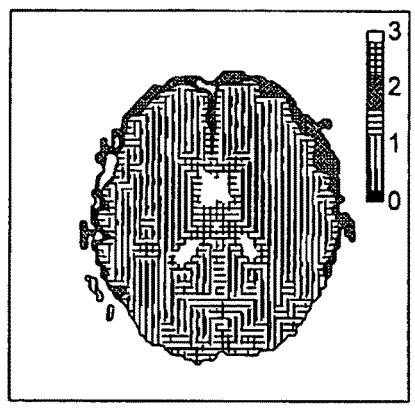
F I G. 6A
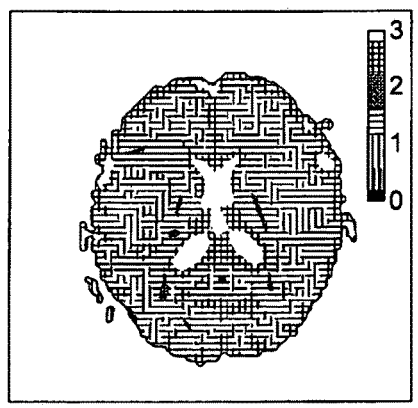
F I G. 6B
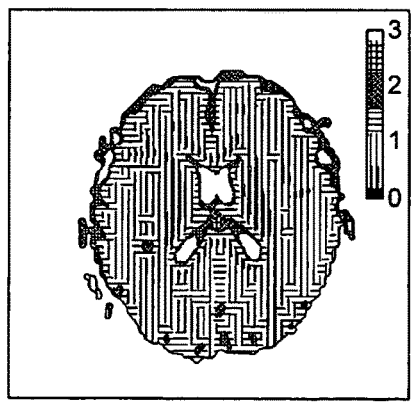
F I G. 6C
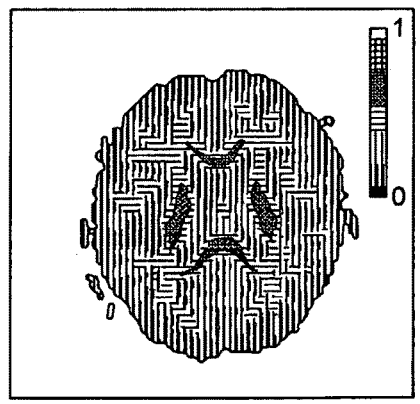
F I G. 6D

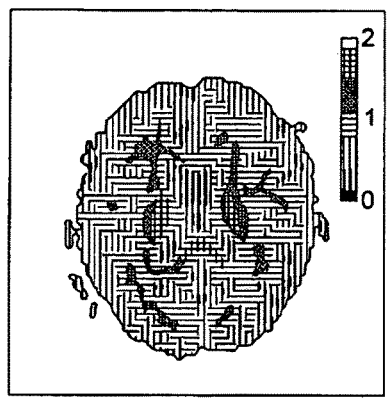 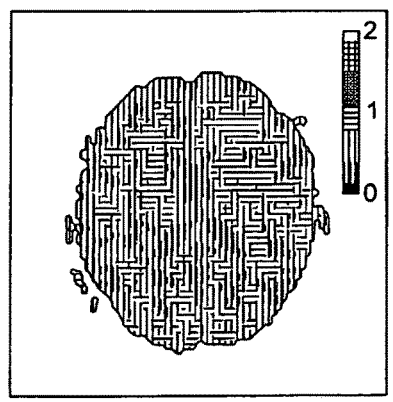
F I G. 7A      F I G. 7B
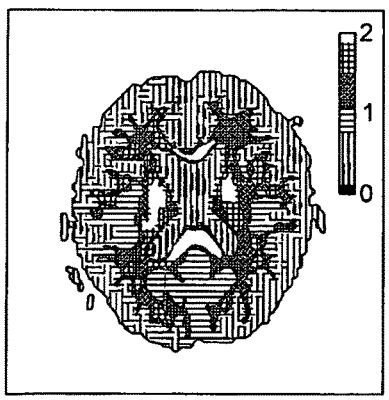
F I G. 7C

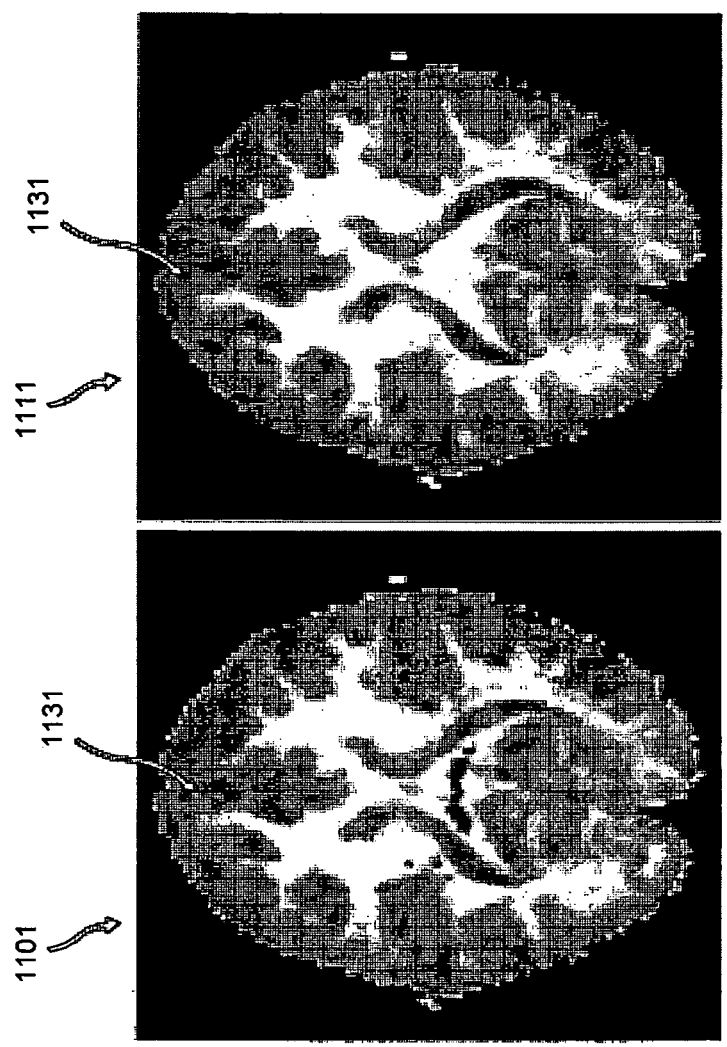

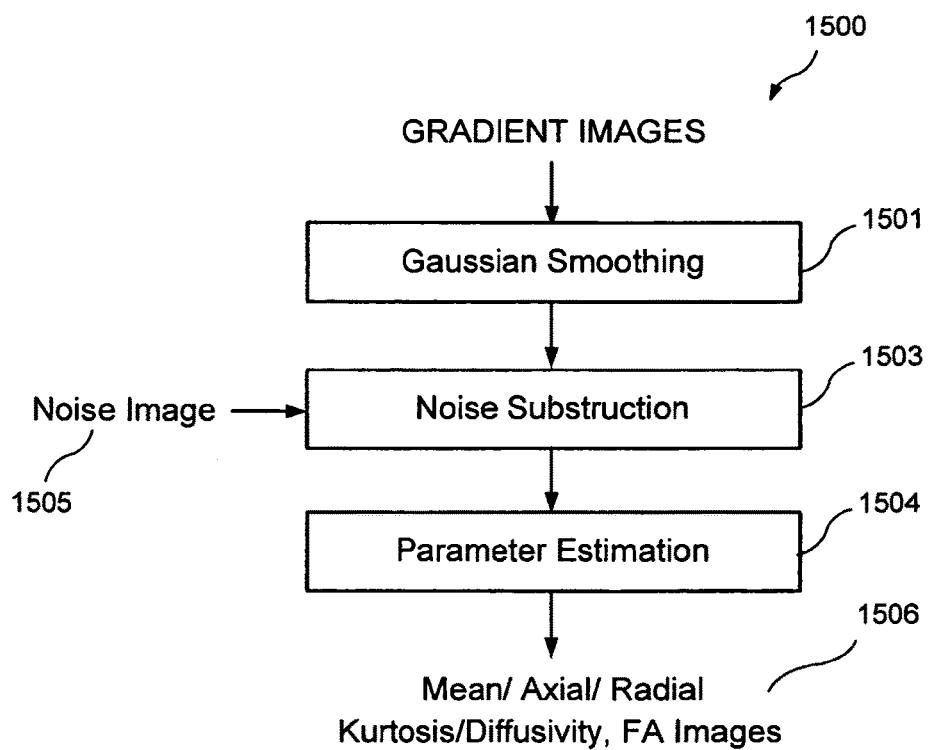
F I G. 15

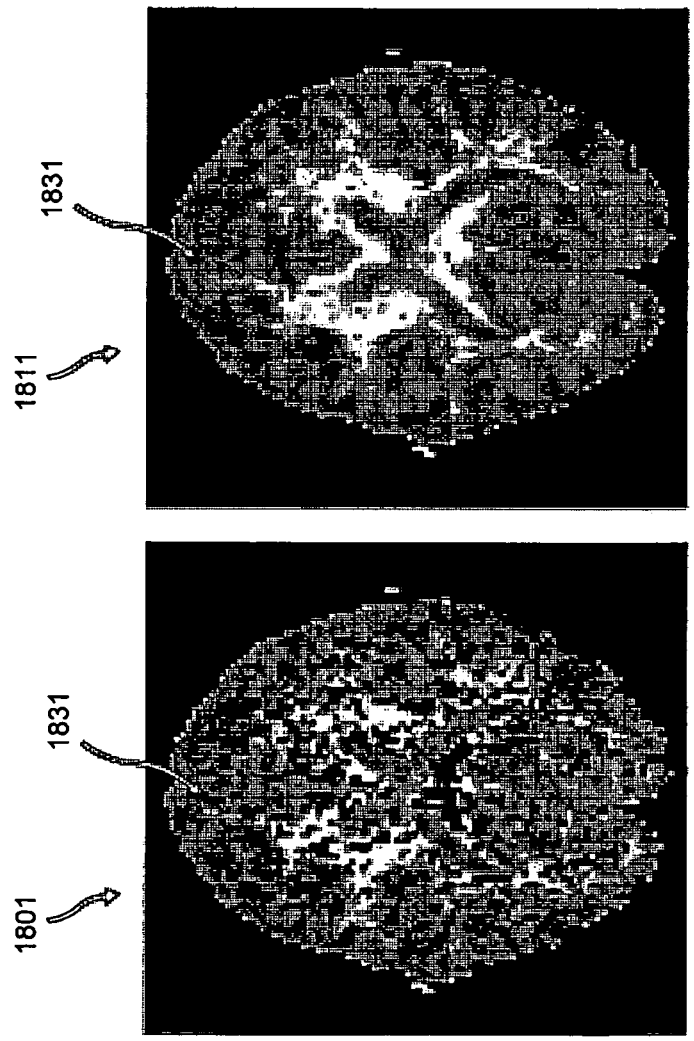

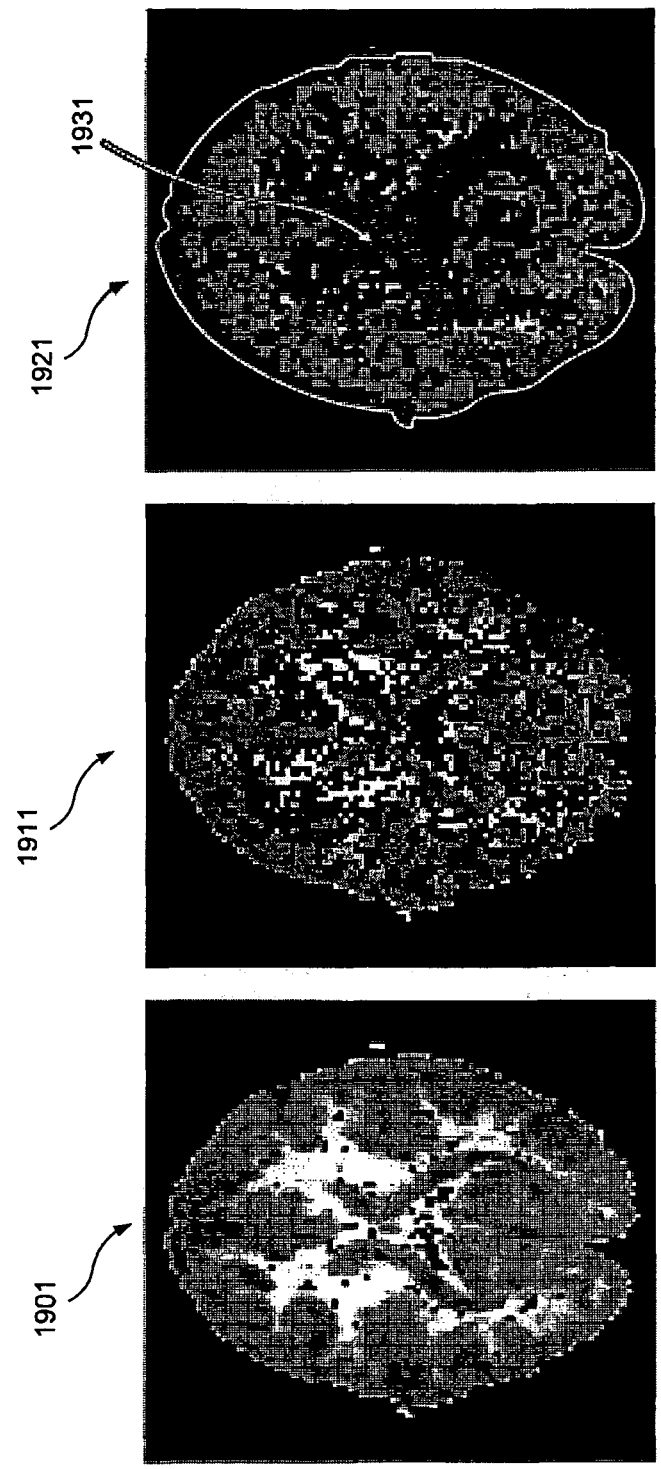

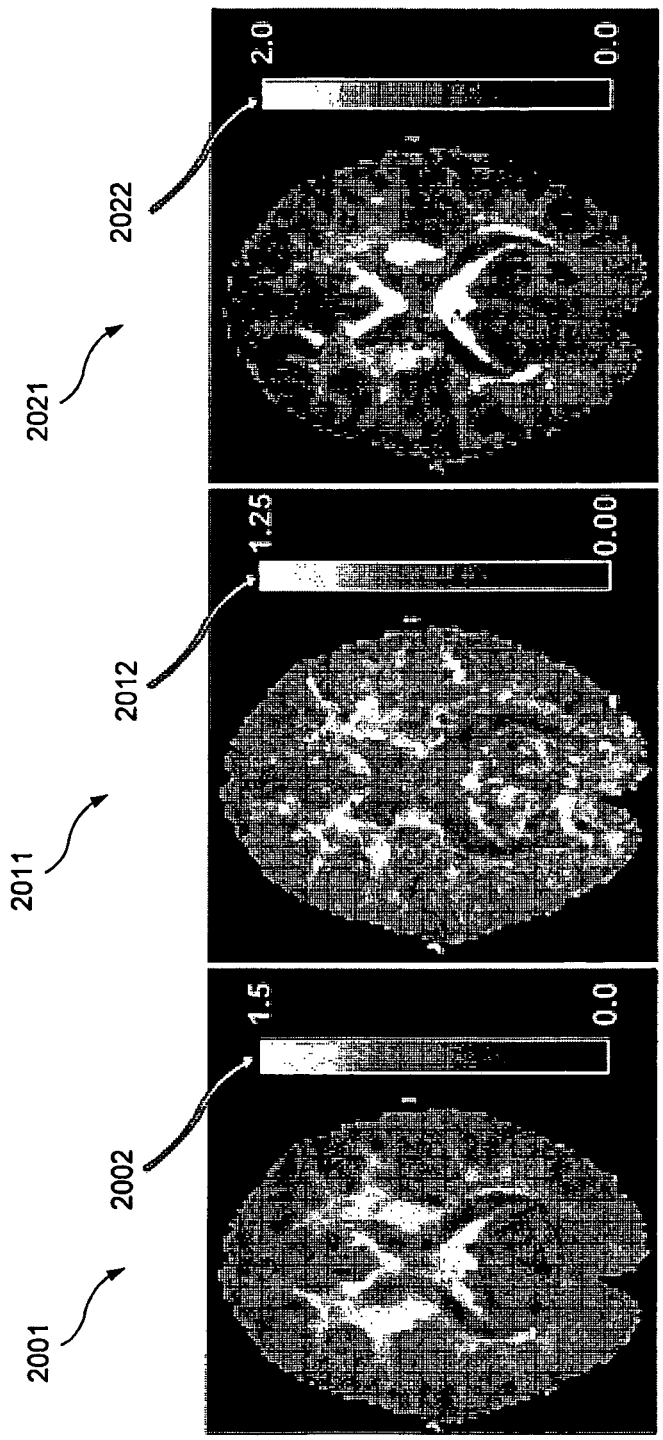
F I G. 20C
F I G. 20B
F I G. 20A

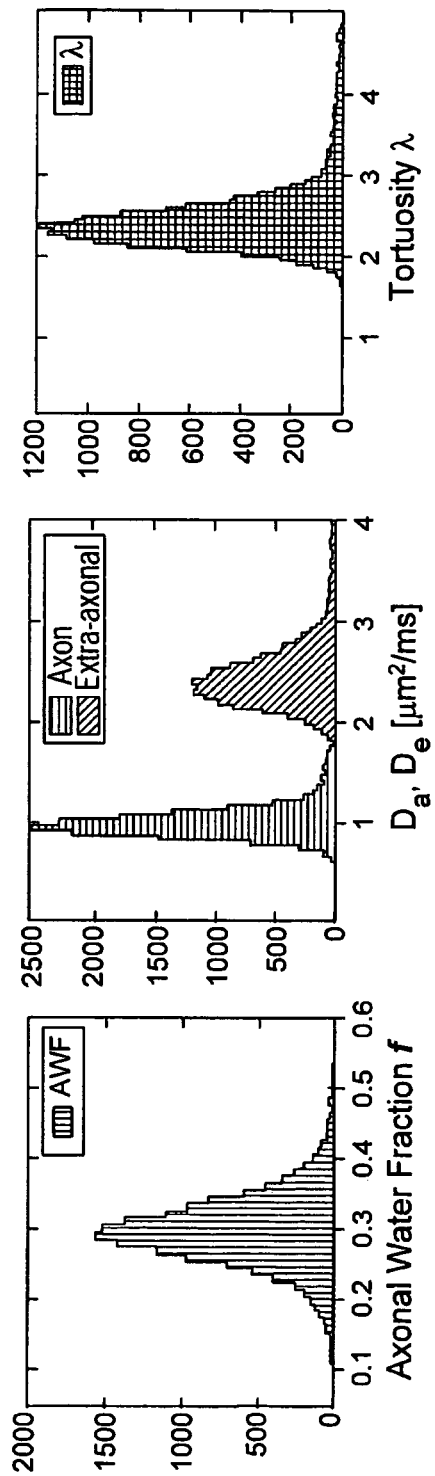

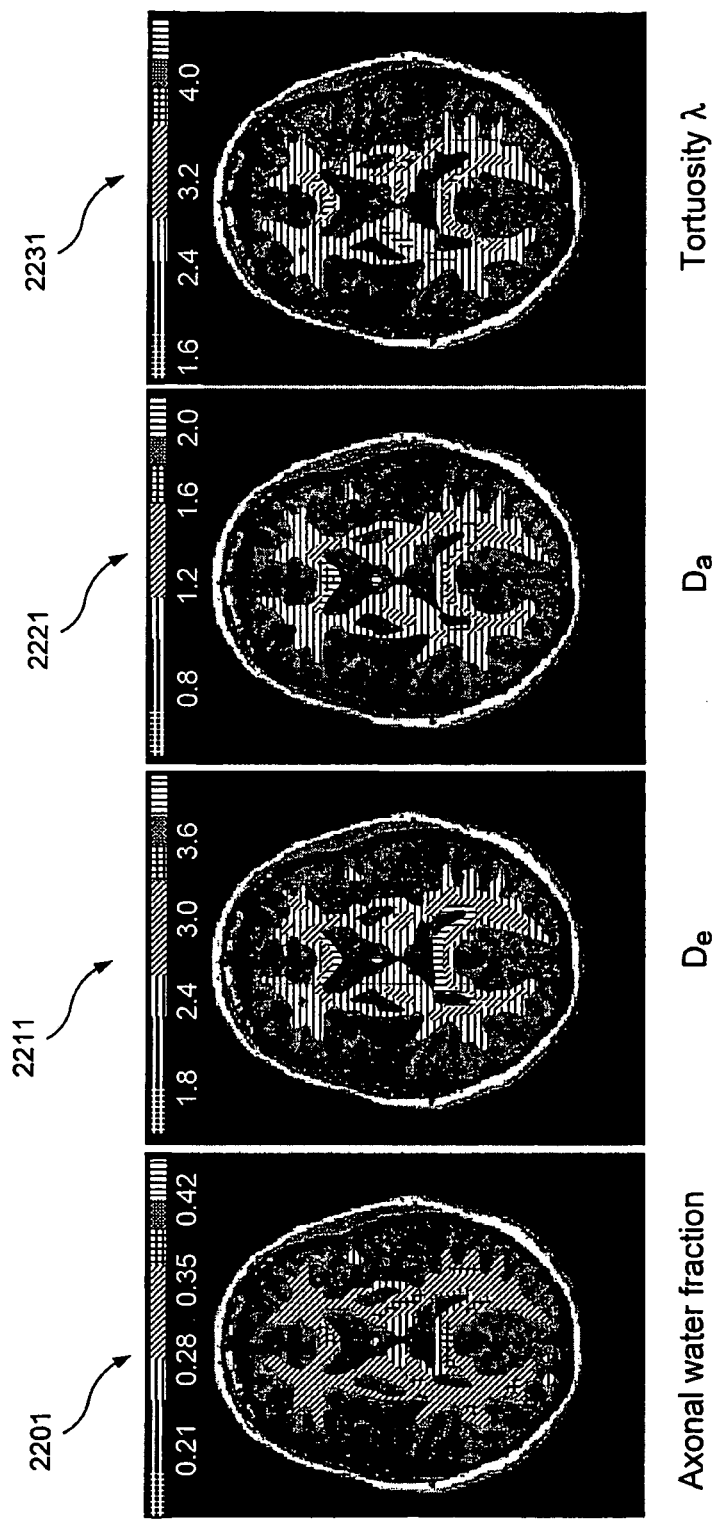
FIG. 22A  Axonal water fraction
FIG. 22B  $D_e$
FIG. 22C  $D_a$
FIG. 22D  Tortuosity $\lambda$

SYSTEM, METHOD AND COMPUTER ACCESSIBLE MEDIUM FOR PROVIDING REAL-TIME DIFFUSIONAL KURTOSIS IMAGING AND FOR FACILITATING ESTIMATION OF TENSORS AND TENSOR-DERIVED MEASURES IN DIFFUSIONAL KURTOSIS IMAGING

CROSS-REFERENCE TO RELATED APPLICATIONS

The present is a continuation of U.S. patent application Ser. No. 13/022,488 filed Feb. 7, 2011, which is a continuation-in-part of International Application No. PCTUS2009/053223 filed Aug. 7, 2009, and relates to and claims priority from U.S. Patent Application Ser. No. 61/087,111 filed Aug. 7, 2008 and U.S. Patent Application Ser. No. 61/325,283 filed Apr. 16, 2010, the entire disclosures of which are hereby incorporated herein by reference.

STATEMENT REGARDING FEDERALLY SPONSORED RESEARCH

The present disclosure was developed, at least in part, using Government support under Grant Nos. NIH R01AG027852, NIH R01EB007656, NIH R01NS039135 and NIH R03MH076180, awarded by the National Institutes of Health. Therefore, the Federal Government may have certain rights in the invention.

FIELD OF THE DISCLOSURE

The present disclosure relates to exemplary embodiments of systems, methods and computer-accessible mediums for providing real-time diffusional kurtosis imaging.

BACKGROUND INFORMATION

Diffusion anisotropy of water in biological tissues can be conventionally quantified with the diffusion tensor (DT) and related indices such as the fractional anisotropy. DT can describe the diffusion displacement probability using a Gaussian distribution function. One of the main applications of the DT is tracing the white matter pathways in the brain using local estimates of the fiber orientations. However, in regions with complex fiber configurations, DT likely fails to describe the full directional information of the diffusion process. Most notably, the DT is not able to resolve fiber crossing, which occurs in many brain regions. A more complete depiction of the water diffusion displacement is given by the probability density function (PDF). PDF can be approximated using q-space imaging techniques, but these techniques require diffusion measurements for a large range of diffusion weightings and diffusion directions. To overcome these limitations, an orientation distribution function (ODF) has been provided for diffusion displacement probability distribution.

Several approaches have been proposed to estimate the ODF. One such approach is the q-ball imaging (QBI), which is based on a Funk transform of high angular resolution diffusion imaging (HARDI) data. The QBI approach has been extended to explore the spherical harmonic basis functions and multiple wavevector fusion. For brain imaging, each of these techniques has several limitations including the need for high b values (i.e., 3000 s/mm² or above) and a large number of encoding directions or the assumption of specific diffusion properties for the investigated fiber populations.

Diffusional kurtosis is a quantitative measure of the degree to which the diffusion displacement probability distribution deviates from a Gaussian form. Diffusional Kurtosis Imaging (DKI) is a magnetic resonance imaging (MRI) technique for measuring this quantity. However, conventional DKI methods require substantial time (approximately 1 hour or more) for post-processing of the acquired images which may be a significant disadvantage in clinical practice.

Further, diffusion of water molecules in biological tissues can be conventionally quantified via diffusion tensor imaging (DTI). (See, e.g., Basser P J, Mattiello J, LeBihan D., *MR diffusion tensor spectroscopy and imaging*, Biophysical Journal 66:259-267 (1994)). DTI can be a valuable tool for noninvasive characterization of tissue microstructural properties (See, e.g., Basser P J., *Inferring microstructural features and the physiological state of tissues from diffusion-weighted images*, NMR in Biomedicine 8:333-3442-3 (1995); and Basser P J, Pierpaoli C., *Microstructural and physiological features of tissues elucidated by quantitative-diffusion-tensor MRI*, Journal of Magnetic Resonance B 111:209-219 (1996)). The DTI model can use a Gaussian approximation to the probability distribution governing the random displacement of water molecules. In many biological tissues, however, the displacement probability distribution can deviate considerably from a Gaussian form. Diffusional kurtosis imaging (DKI) can be an extension of DTI which can enable the characterization of this deviation by estimating the kurtosis of the displacement distribution (see, e.g., Jensen J H, Helpern J A, *Quantifying non-Gaussian water diffusion by means of pulsed-field-gradient MRI*, In Proceedings of the International Society for Magnetic Resonance in Medicine Annual Meeting, Volume 11, p. 2154, Toronto, Canada (2003); Jensen J H, Helpern J A, Ramani A, Lu H, Kaczynski K, *Diffusional kurtosis imaging: The quantification of non-Gaussian water diffusion by means of magnetic resonance imaging*, Magnetic Resonance in Medicine 53:1432-1440 (2005); and Lu H, Jensen J H, Ramani A, Helpern J A, *Three-dimensional characterization of non-gaussian water diffusion in humans using diffusion kurtosis imaging*, NMR in Biomedicine 19:236-247 (2006)), in addition to the estimation of the standard DTI-derived parameters. DKI has shown promising results in studies of human brain aging (see, e.g., Falangola M F, Jensen J H, Babb J S, Hu C, Castellanos F X, Di Martino A, Ferris S H, Helpern J A, *Age-related non-Gaussian diffusion patterns in the prefrontal brain*, Journal of Magnetic Resonance Imaging 28:1345-1350 (2008)), detection of cerebral gliomas (see, e.g, Raab P, al. e, *Diffusional kurtosis imaging of cerebral gliomas—analysis of microstructural differences*, Radiology, in press (2010)), and rodent brain maturation (see, e.g, Cheung M M, Hui E S, Chan K C, Helpern J A, Qi L, Wu E X, *Does diffusion kurtosis imaging lead to better neural tissue characterization? A rodent brain maturation study*, NeuroImage 45:386-392 (2009)). Moreover, the additional information provided by DKI has been exploited to resolve intravoxel fiber crossings (see, e.g., Lazar M, Jensen J H, Xuan L, Helpern J A, *Estimation of the orientation distribution function from diffusional kurtosis imaging*, Magnetic Resonance in Medicine 60:774-781 (2008)), thus improving upon DTI-based fiber tracking methods, for example.

An exemplary DKI model can be parameterized by the diffusion and kurtosis tensors from which several rotationally-invariant scalar measures can be extracted. The most common tensor-derived measures can be axial, radial, and mean kurtoses (see, e.g., Jensen et al., *Quantifying non-Gaussian water diffusion by means of pulsed-field-gradient MRI* (2003), supra.; Jensen et al, *Diffusional kurtosis imaging: The quantification of non-Gaussian water diffusion by means of magnetic resonance imaging* (2005), supra.; Lu H, supra.; and Hui E S, Cheung M M, Qi L, Wu E X, *Towards better MR characterization of neural tissues using directional diffusion kurtosis analysis*, NeuroImage 42:122-134 (2008)); mean, axial, and radial diffusivity (see, e.g., Basser P J. *Inferring microstructural features and the physiological state of tissues from diffusion-weighted images* (1995), supra.; and Song S-K, Sun S-W, Ramsbottom M J, Chang C, Russell J, Cross A H, *Dysmyelination revealed through MRI as increased radial (but unchanged axial) diffusion of water*, NeuroImage 17(3):1429-1436 (2002)); and fractional anisotropy (FA) (see, e.g., Basser P J. *Inferring microstructural features and the physiological state of tissues from diffusion-weighted images* (1995), supra.).

The interpretability of these metrics can be influenced by the estimation accuracy of the tensors. Noise, motion, and imaging artifacts can introduce errors into the estimated tensors. Sufficiently large errors can cause the tensor estimates to be physically and/or biologically implausible. For instance, the directional diffusivities can become negative, that is, the diffusion tensor can become non-positive definite (NPD). A consequence of NPD diffusion tensor estimates can be that FA values, which should range between 0 and 1, can exceed 1, particularly in high FA regions of the brain such as corpus callosum. (See, e.g., Koay C G, Carew J D, Alexander A L, Basser P J, Meyerand M E, *Investigation of anomalous estimates of tensor-derived quantities in diffusion tensor imaging*, Magnetic Resonance in Medicine 55:930-936 (2006)). Inaccuracies in the estimated diffusion and kurtosis tensors can also drive the estimated directional kurtoses outside of an acceptable range. Empirical evidence in the brain as well as idealized multi-compartment diffusion models suggest that directional kurtoses can be typically positive and also do not exceed a certain level depending on tissue complexity. (See, e.g., Jensen et al, *Diffusional kurtosis imaging: The quantification of non-Gaussian water diffusion by means of magnetic resonance imaging* (2005), supra.) The maximum allowable kurtosis can also be influenced by the maximum b-value used in image acquisition. (Id.).

Exemplary diffusion and kurtosis tensors were estimated using unconstrained nonlinear least squares (UNLS). (See, e.g., Lu H et al., *Three-dimensional characterization of non-gaussian water diffusion in humans using diffusion kurtosis imaging* (2006), supra.) In a related work, higher-order diffusion tensors were estimated using unconstrained linear least squares (ULLS). (See, e.g., Liu C, Bammer R, Acar B, Moseley M E, *Characterizing non-Gaussian diffusion by using generalized diffusion tensors*, Magnetic Resonance in Medicine 51:924-937 (2004)). These unconstrained schemes do not guarantee acceptable tensor estimates. To address this drawback in the context of DTI, the Cholesky decomposition has been utilized to impose the non-negative definiteness constraint on the diffusion tensor (see, e.g., Koay C G, Carew J D, Alexander A L, Basser P J, Meyerand M E, *Investigation of anomalous estimates of tensor-derived quantities in diffusion tensor imaging*, Magnetic Resonance in Medicine 55:930-93613, 15 (2006); and Wang Z, Vemuri B C, Chen Y, Mareci T H, *A Constrained variational principle for direct estimation and smoothing of the diffusion tensor field from complex DWI*, IEEE Transactions on Medical Imaging 23:930-939 (2004)) using either the ULLS or UNLS algorithms. Moreover, a parameterization has been exemplary in a UNLS framework to guarantee a positive diffusivity function in a fourth-order tensor-only model of diffusion. (See, e.g., Barmpoutis A, Hwang M S, Howland D, Forder J R, Vemuri B C, *Regularized positive-definite fourth order tensor field estimation from DW-MRI*, NeuroImage 45:S153-S162 (2009)).

Thus, there is a likely need for a tractable formulation of the tensor estimation problem in DKI, wherein the constraints on acceptable diffusivity and kurtosis parameters can be conveniently imposed. The estimation problem can be cast as linear least squares (LS) subject to linear constraints. The exemplary constrained linear LS (CLLS) formulation yields a convex objective function that avoids the problem of local minima, and permits efficient solutions via convex quadratic programming or a fast heuristic algorithm. The constraints ensure non-negative diffusivity along the imaged gradient directions, as well as guaranteeing that the directional kurtoses can be within a physically and biologically plausible range. The two algorithms exemplary for solving the CLLS problem strike different tradeoffs between the speed and accuracy of the solution as well as algorithm flexibility. The quadratic programming-based (CLLS-QP) algorithm exactly satisfies the constraints and can also handle an arbitrary number of diffusion weightings and different gradient sets for each diffusion weighting, but it does so at a moderately high computational cost. On the contrary, the heuristic (CLLS-H) algorithm produces an approximation to the optimal solution, but it accomplishes this at almost no computational overhead compared to the ULLS.

Thus, it can be desirable to provide exemplary embodiments of method, system and computer accessible medium for providing real-time diffusional kurtosis imaging, and to estimate the orientation distribution function, which can reduce or avoid at least some of the problems encountered by the conventional techniques as set out above.

SUMMARY OF EXEMPLARY EMBODIMENTS OF DISCLOSURE

At least some of the above described problems can be addressed by exemplary embodiments of the system, method and computer-accessible (e.g., non-transitory and/or hardware) medium according to the present disclosure. For example, using such exemplary embodiments, it is possible to provide a method for determining a measure of diffusional kurtosis. which comprises receiving data relating to at least one diffusion weighted image, and using a computer arrangement, determining a measure of a diffusional kurtosis as a function of the received data using a closed form solution procedure. The method can further comprise performing (i) providing the measure of the diffusional kurtosis to a display device, and/or (ii) recording the measure of the diffusional kurtosis. At least one diffusion weighted image can be acquired for three or more b-values. Such one or more diffusion weighted images can be acquired for 15 or more gradient directions.

The measure of the diffusional kurtosis can be determined using a mean kurtosis procedure. The mean kurtosis can be determined by averaging measures of a diffusion and a kurtosis over each gradient direction. The closed form solution procedure can include at least one or more elliptic integrals, and such one or more elliptic integrals can be associated with eigenvalues of at least one diffusion tensor based on the at least one diffusion weighted image. Such one or more elliptic integrals can be associated with at least one Carlson symmetric form of an elliptic integral.

The measure of the diffusional kurtosis can be an axial kurtosis and/or a radial kurtosis. At least a portion of the received data can relate to at least one orientation distribution function, the portion of the received data being calculated using the measure of the diffusional kurtosis. The exemplary method can further comprise resolving at least one fiber crossing using the received data from the at least one orientation distribution function. Such one or more fibers crossing can be a crossing of at least one of two fibers, three fibers or four fibers.

The exemplary method can further comprise providing a directional color map of the at least one fiber crossing, whereas the directional color map can provide fiber direction estimates as a function of the data associated with the orientation distribution function(s). A fiber tractography can be performed using the data associated with the orientation distribution function(s).

The exemplary method can further comprise analyzing white matter connectivity patterns using the data associated with the at least one orientation distribution function, and estimating white matter pathways using the data associated with the at least one orientation distribution function. The exemplary method can further comprise analyzing fibers tracts which at least one of cross, kiss, branch, merge or splay, using the data associated with the orientation distribution function(s).

The received data associated with the orientation distribution function(s) can include Gaussian diffusion contributions and substantially exclude non-Gaussian diffusion contributions, include non-Gaussian diffusion contributions and substantially exclude Gaussian diffusion contributions or include Gaussian diffusion contributions and non-Gaussian diffusion contributions.

The data associated with the orientation distribution function(s) can be an approximation of an integral of a function depending on diffusion and kurtosis coefficients over a perpendicularly-oriented great circle.

The exemplary method can further comprise assessing at least one medical condition of a subject using the measure of the diffusional kurtosis. The medical condition(s) can be a neurological disease and/or a neuro-degenerative diseases. The medical condition(s) can be Alzheimer's disease, stroke, head trauma, attention deficit hyperactivity disorder and/or schizophrenia. The medical condition(s) can be assessed by comparing further data relating to the subject with predetermined control data, and the control data can comprise age-matched control data.

The exemplary method can further comprise determining a measure of a diffusional restrictivity using the measure of the diffusional kurtosis. The measure of the diffusional restrictivity can be determined from a diffusion tensor and a kurtosis tensor relating to the diffusion weighted image(s). The measure of the diffusional restrictivity can include a measure of Gaussian restrictivity which substantially excludes non-Gaussian restrictivity, include a measure of non-Gaussian restrictivity which substantially excludes Gaussian restrictivity, or include a measure of Gaussian restrictivity and non-Gaussian restrictivity.

The measure of diffusional restrictivity can be determined using a first measure dependent on diffusivity and a second measure dependent on diffusional kurtosis. The second measure can reflect non-Gaussian diffusion contributions to a diffusion signal.

The exemplary method can further comprise identifying at least one region of interest in an anatomical structure based on the measure of the diffusional kurtosis and/or the measure of the diffusional restrictivity. The anatomical structure can comprise a brain tissue. The at least one region of interest can indicate differences in microstructure between different portions of the anatomical structure. The region(s) of interest can at least partially distinguish between a reversibly injured tissue and an irreversibly injured tissue.

Using such exemplary embodiments, it is also possible to provide the system for determining a measure of diffusional kurtosis comprising a first arrangement configured to receive data relating to at least one diffusion weighted image, and a second arrangement configured to determine a measure of a diffusional kurtosis as a function of the received data using a closed form solution procedure. The second arrangement can be further configured to perform (i) provide the measure of the diffusional kurtosis to a display device, and/or (ii) record the measure of the diffusional kurtosis. The diffusion weighted image(s) can be acquired for three or more b-values, and the diffusion weighted image(s) can be acquired for 15 or more gradient directions.

The second arrangement can be further configured to assess at least one medical condition of a subject using the measure of the diffusional kurtosis, and can be further configured to determine a measure of a diffusional restrictivity using the measure of the diffusional kurtosis. The second arrangement can be further configured to identify at least one region of interest in an anatomical structure based on the measure of the diffusional kurtosis and/or the measure of the diffusional restrictivity.

Using such exemplary embodiments, it is also possible to provide the computer-accessible medium for determining a measure of diffusional kurtosis, the computer-accessible medium including instructions thereon, wherein, when a computing arrangement executes the instructions, the computing arrangement is configured to perform procedures comprising receiving data relating to at least one diffusion weighted image, and determining a measure of a diffusional kurtosis as a function of the received data using a closed form solution procedure. The computing arrangement can be further configured to (i) provide the measure of the diffusional kurtosis to a display device, and/or (ii) record the measure of the diffusional kurtosis.

Exemplary embodiments associated with exact expressions for radial and mean kurtoses according to the present disclosure are also described herein. Exemplary embodiments of mean kurtosis (MK) have been estimated as the average of directional kurtoses (4-6), whereas the analytical expression given here is an explicit function of the diffusion and kurtosis tensors. Exemplary definition of radial kurtosis (RK) can be different from that of (11), in that the RK presented here is defined as the diffusional kurtosis averaged over all directions perpendicular to the diffusion tensor eigenvector with the largest eigenvalue.

Further, described herein is an exemplary embodiment according to the present disclosure of an idealized diffusion model of white matter (WM) that can be used for, e.g., DKI analysis, which can allow for quantification of the intra- and extra-axonal diffusivities, the axonal water fraction and the tortuosity of the extra-axonal space, for example. Exemplary embodiments according to the present disclosure can also provide a physical interpretation of DKI metrics for WM, for example.

These and other objects, features and advantages of the present disclosure will become apparent upon reading the following detailed description of embodiments of the present disclosure, when taken in conjunction with the appended claims.

BRIEF DESCRIPTION OF THE DRAWINGS

The foregoing and other exemplary objects of the present disclosure will be apparent upon consideration of the following detailed description, taken in conjunction with the accompanying exemplary drawings and claims, in which like reference characters refer to like parts throughout, and in which:

FIGS. 1(a)-1(f) are illustrations of exemplary three dimensional surfaces of exact and estimated ODF's for exemplary diffusion models, in accordance with certain exemplary embodiments of the present disclosure;

FIGS. 2(a)-2(f) are illustrations of further exemplary three dimensional surfaces of exact and estimated ODF's for the exemplary diffusion models, in accordance with certain exemplary embodiments of the present disclosure;

FIGS. 5(a)-5(d) are is illustrations of the exemplary ODF maps of the intersection between the posterior region of the superior longitudinal fasciculus with the projection fibers of the corona radiata and the posterior transverse association fibers, in accordance with certain exemplary embodiments of the present disclosure;

FIGS. 6(a)-6(d) are illustrations of exemplary brain images of a mean diffusivity, axial diffusivity, radial diffusivity and a fractional anisotropy, respectively, provided by conventional diffusion tensor imaging, in accordance with certain exemplary embodiments of the present disclosure;

FIGS. 7(a)-7(c) are illustrations of exemplary parametric maps derived with real-time diffusional kurtosis imaging obtained using certain exemplary embodiments of the present disclosure;

FIG. 11(a) is an illustration of an exemplary image map produced with ULLS, in accordance with certain exemplary embodiments of the present disclosure;

FIG. 11(b) is an illustration of an exemplary image map produced with an exemplary embodiment of CLLS, in accordance with certain exemplary embodiments of the present disclosure;

FIG. 15 is an illustration of an exemplary processing pipeline for the estimation of tensor-derived parameters, in accordance with certain exemplary embodiments of the present disclosure;

FIG. 18(a) is an exemplary MK image obtained using 6 gradient directions for b=1000 s/mm$^2$ and 30 gradient directions for b=2000 s/mm$^2$ and ULLS, in accordance with certain exemplary embodiments of the present disclosure;

FIG. 18(b) is another exemplary MK image also obtained using 6 gradient directions for b=1000 s/mm$^2$ and 30 gradient directions for b=2000 s/mm$^2$ and CLLS-QP, in accordance with other exemplary embodiments of the present disclosure;

FIG. 19(a) is a still another exemplary image of voxels where the diffusion and kurtosis tensors estimated using ULLS again violate the constraints on directional diffusivities, in accordance with still further exemplary embodiments of the present disclosure;

FIG. 19(b) is a further exemplary image of voxels where the diffusion and kurtosis tensors estimated using ULLS yet again violate the constraints on minimum directional kurtoses, in accordance with additional exemplary embodiments of the present disclosure;

FIG. 19(c) is a still further exemplary image of voxels where the diffusion and kurtosis tensors estimated using ULLS again violate the constraints on maximum directional kurtoses, in accordance with still other exemplary embodiments of the present disclosure;

FIG. 20(a) is an additional exemplary MK Kurtosis map estimated using 30 gradient directions for b=1000, 2000 s/mm$^2$, utilizing an exemplary CLLS-QP procedure and exact expressions for the kurtoses, in accordance with yet further exemplary embodiments of the present disclosure;

FIG. 20(b) is a still further exemplary AK Kurtosis map estimated using 30 gradient directions for b=1000, 2000 s/mm$^2$, also utilizing an exemplary CLLS-QP procedure and exact expressions for the kurtoses, in accordance with other exemplary embodiments of the present disclosure;

FIG. 20(c) is an exemplary RK Kurtosis map estimated using 30 gradient directions for b=1000, 2000 s/mm$^2$, utilizing an exemplary CLLS-QP procedure and exact expressions for the kurtoses, in accordance with certain exemplary embodiments of the present disclosure;

FIG. 21(a) is an exemplary histogram for Axonal Water Fraction f derived from WM voxels, in accordance with certain exemplary embodiments of the present disclosure;

FIG. 21(b) is an exemplary histogram for xonal diffusivity $D_a$ and extra-axonal diffusivity $D_e$ derived from WM voxels, in accordance with certain exemplary embodiments of the present disclosure;

FIG. 21(c) is an exemplary histogram for tortuosity $\lambda$ derived from WM voxels, in accordance with certain exemplary embodiments of the present disclosure;

FIG. 22(a) is an exemplary parametric coronal image overlayed on a MPRAGE image with Axonal Water Fraction f, in accordance with certain exemplary embodiments of the present disclosure;

FIG. 22(b) is an exemplary parametric coronal image overlayed on a MPRAGE image with axonal diffusivity $D_a$, in accordance with certain exemplary embodiments of the present disclosure;

FIG. 22(c) is an exemplary parametric coronal image overlayed on a MPRAGE image with the extra-axonal diffusivity $D_e$, in accordance with certain exemplary embodiments of the present disclosure; and FIG. 22(d) is an exemplary parametric coronal image overlayed on a MPRAGE image with the tortuosity $\lambda$, in accordance with certain exemplary embodiments of the present disclosure.

Figure 3B:
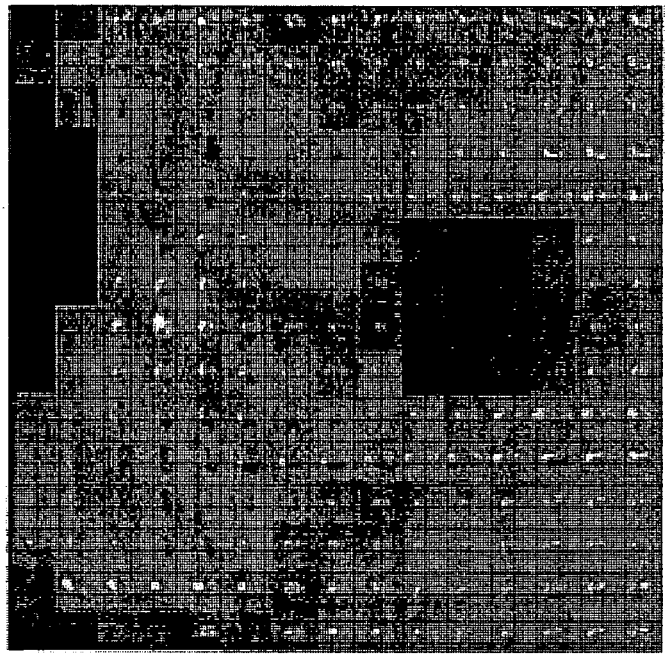
FIGS. 3(a)-3(e) are illustrations of exemplary ODF maps of the brainstem, in accordance with certain exemplary embodiments of the present disclosure.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject disclosure.

DETAILED DESCRIPTION OF EXEMPLARY EMBODIMENTS OF DISCLOSURE

Exemplary embodiments of the methodologies and procedures according to the present disclosure which can be implemented by the exemplary embodiments of system, method and computer-accessible medium according to the present disclosure will now be described, at least to some extent, with reference to the figures.

Diffusional Kurtosis Imaging (DKI) is an exemplary magnetic resonance imaging technique, which can be useful for the assessment of a variety of diseases including stroke, Alzheimer's disease, head trauma, schizophrenia and attention deficit hyperactivity disorder. In evaluating acute stroke processed DKI, results should ideally be available on-line within seconds after the scanning so that timely treatment decisions can be made. Real-time DKI analysis routinely available on commercial Magnetic Resonance Imaging (MRI) scanners would also greatly facilitate the application and increase the usefulness of DKI for many other diseases. "Real-time" can comprise but is not limited to, e.g., an analysis in which results, measurements, etc. are obtained within approximately one minute, and sometimes within approximately 30 seconds.

In the exemplary embodiments of the present disclosure, real-time DKI method, system and computer-accessible medium can be provided, which can be based both on a particular data acquisition scheme and on a mathematical prescription for rapid analysis of the images.

Exemplary Data Acquisition Procedure(s)

An exemplary DKI data set utilizes that diffusion-weighted (DW) images can be acquired for approximately 3 or more b-values and approximately 15 or more gradient directions. A b-value is a factor of diffusion weighted sequences, and summarizes the influence of the gradients on diffusion weighted images. The higher the b-value, the stronger the diffusion weighting. Particularly, there can be an advantage in using precisely 3 b-values in that this can allow one to avoid numerical nonlinear fitting procedures which are both time-consuming and often suffer from convergence problems. In this exemplary manner, the post-processing time can be significantly reduced. An exemplary choice of b-values for brain imaging can be b=0, 1000, 2000 (s/mm$^2$), but the exemplary embodiments of the present disclosure is not restricted to these exemplary values. The gradient directions can typically be distributed uniformly on a sphere. An exemplary selection can be a set of 30 directions defined by a truncated icosahedron. For each exemplary b-value and direction, one or more images may be acquired. If more than one image is acquired, such exemplary images can be co-registered and averaged prior to data processing.

A first exemplary procedure in the exemplary data processing methodology can be to determine the diffusion coefficient ($D_i$) and diffusional kurtosis ($k_i$) for the ith gradient direction in each voxel. Voxels can be processed independently according to the same or similar procedure, and so it can be sufficient to describe the procedure for a single voxel. An exemplary closed form solution can be used to determine a measure of diffusional kurtosis, as will be set out below. An equation or system of equations can have a closed-form solution, e.g., when at least one solution can be expressed as a closed-form expression. A closed-form expression can, e.g., be expressed analytically in terms of a bounded number of certain functions.

If the DW signal intensity corresponds to an ith direction for a given voxel and a b-value is indicated by $S_i(b)$, then:

$$D_i = \frac{(b_3 + b_1)D_i^{(12)} - (b_2 + b_1)D_i^{(13)}}{b_3 - b_2} \qquad [1]$$

$$K_i = 6\frac{D_i^{(12)} - D_i^{(13)}}{(b_3 - b_2)D_i^2} \qquad [2]$$

where $$D_i^{(12)} \equiv \frac{\ln\left[\frac{S_i(b_1)}{S_i(b_2)}\right]}{b_2 - b_1}, \qquad D_i^{(13)} \equiv \frac{\ln\left[\frac{S_i(b_1)}{S_i(b_3)}\right]}{b_3 - b_1}, \qquad [3]$$

and $b_1$, $b_2$, $b_3$ represent the three b-values used for data acquisition.

In one exemplary procedure, from the set of $D_i$ and $K_i$, the diffusion tensor and the diffusional kurtosis tensor can be constructed by linear inversion. The exemplary linear system for the diffusion tensor can be represented by:

$$\begin{pmatrix} D_1 \\ D_2 \\ \vdots \\ D_N \end{pmatrix} = \qquad [4]$$

-continued $$\begin{pmatrix} [g_1^{(1)}]^2 & [g_2^{(1)}]^2 & [g_3^{(1)}]^2 & 2g_1^{(1)}g_2^{(1)} & 2g_1^{(1)}g_3^{(1)} & 2g_2^{(1)}g_3^{(1)} \\ [g_1^{(2)}]^2 & [g_2^{(2)}]^2 & [g_3^{(2)}]^2 & 2g_1^{(2)}g_2^{(2)} & 2g_1^{(2)}g_3^{(2)} & 2g_2^{(2)}g_3^{(2)} \\ \vdots & \vdots & \vdots & \vdots & \vdots & \vdots \\ [g_1^{(N)}]^2 & [g_2^{(N)}]^2 & [g_3^{(N)}]^2 & 2g_1^{(N)}g_2^{(N)} & 2g_1^{(N)}g_3^{(N)} & 2g_2^{(N)}g_3^{(N)} \end{pmatrix} \begin{pmatrix} D_{11} \\ D_{22} \\ D_{33} \\ D_{12} \\ D_{13} \\ D_{23} \end{pmatrix}$$

where N can be the number of gradient directions, $g_i^{(n)}$ can be the ith component of the nth gradient direction vector ($|g|=1$), and $D_{ij}$ can be the components of the diffusion tensor. The linear system for the diffusional kurtosis tensor can then be represented by:

$$\begin{pmatrix} D_1^2 K_1 \\ D_2^2 K_2 \\ \vdots \\ D_N^2 K_N \end{pmatrix} = \overline{D}^2 \begin{pmatrix} [g_1^{(1)}]^4 & \ldots & 4[g_1^{(1)}]^3 g_2^{(1)} & \ldots & 6[g_1^{(1)}]^2 [g_2^{(1)}]^2 & \ldots & 12g_1^{(1)} g_2^{(1)} [g_3^{(1)}]^2 \\ [g_1^{(2)}]^4 & \ldots & 4[g_1^{(2)}]^3 g_2^{(2)} & \ldots & 6[g_1^{(2)}]^2 [g_2^{(2)}]^2 & \ldots & 12g_1^{(2)} g_2^{(2)} [g_3^{(2)}]^2 \\ \vdots & \vdots & \vdots & \vdots & \vdots & \vdots & \vdots \\ [g_1^{(N)}]^4 & \ldots & 4[g_1^{(N)}]^3 g_2^{(N)} & \ldots & 6[g_1^{(N)}]^2 [g_2^{(N)}]^2 & \ldots & 12g_1^{(N)} g_2^{(N)} [g_3^{(N)}]^2 \end{pmatrix} \begin{pmatrix} W_{1111} \\ W_{2222} \\ W_{3333} \\ W_{1112} \\ W_{1113} \\ W_{1222} \\ W_{1333} \\ W_{2223} \\ W_{1122} \\ W_{1133} \\ W_{2233} \\ W_{2333} \\ W_{1123} \\ W_{1223} \\ W_{1233} \end{pmatrix}, \quad [5]$$

where $W_{ijkl}$ can be the components of the diffusional kurtosis tensor and D can be the mean diffusivity (MD) which may be calculated from $$\overline{D} = \tfrac{1}{3}(D_{11}+D_{22}+D_{33}) \qquad [6]$$

Both $D_{ij}$ and $W_{ijkl}$ can be symmetric with respect to permutation of their indices so that these tensors are determined by the components appearing in exemplary Equations [4] and [5]. These two exemplary linear systems can be readily solved by an exemplary method which can utilize a singular value decomposition. Since the matrices for the two exemplary linear systems can depend on the gradient directions, their singular value decompositions can be calculated once for any particular choice of directions. Accordingly, this exemplary procedure in the data processing would require minimal computational time.

For additional exemplary processing, it can be convenient to rotate to a reference frame (the eigenframe) in which the diffusion tensor is diagonal. In the eigenframe, the diffusion tensor can takes the form of:

$$\tilde{D}_{ij} = \lambda_i \delta_{ij}, \qquad [7]$$

where $\lambda_i$ can be the eigenvalues and $\delta_{ij}$ can be the kronecker delta, and the diffusional kurtosis tensor can take the form of:

$$\tilde{W}_{ijkl} = \sum_{i',j',k',l'} R_{ii'} R_{jj'} R_{kk'} R_{ll'} W_{i'j'k'l'} \qquad [8]$$

with $R_{ij}$ being the rotation matrix and the sums being carried out from exemplary Equations 1 to 3 provided herein. The exemplary rotation matrix can be given by:

$$R_{ij} = u_j^{(i)} \qquad [9]$$

where $u_j^{(i)}$ can be the jth component of the ith eigenvector for $D_{ij}$. The eigenvalues and eigenvectors can be determined by using any of several exemplary standard techniques, such as Jacobi's method. Without loss of generality, it is possible to order the eigenvalues so that ($\lambda_1 \leq \lambda_2 \leq \lambda_3$).

From the diffusion tensor eigenvalues, the axial diffusivity can be obtained by:

$$D_\parallel = \lambda_3, \qquad [10]$$

and the radial diffusivity:

$$D_\perp = \tfrac{1}{2}(\lambda_1 + \lambda_2). \qquad [11]$$

It is also possible to determine the fractional anisotropy (FA) as follows:

$$FA = \sqrt{\frac{(\lambda_1 - \lambda_2)^2 + (\lambda_1 - \lambda_3)^2 + (\lambda_2 - \lambda_3)^2}{2(\lambda_1^2 + \lambda_2^2 + \lambda_3^2)}} \qquad [12]$$

From the eigenframe representation of the diffusional kurtosis tensor, the mean kurtosis (MK) can be calculated as follows:

$$\overline{K} = 6A_{1122}(\lambda_1, \lambda_2, \lambda_3) \tilde{W}_{1122} + 6A_{1122}(\lambda_1, \lambda_3, \lambda_2) \tilde{W}_{1133} + \qquad [13]$$
$$6A_{1122}(\lambda_2, \lambda_3, \lambda_1) \tilde{W}_{2233} + A_{3333}(\lambda_2, \lambda_3, \lambda_1) \tilde{W}_{1111} +$$
$$A_{3333}(\lambda_1, \lambda_3, \lambda_2) \tilde{W}_{2222} + A_{3333}(\lambda_1, \lambda_2, \lambda_3) \tilde{W}_{3333},$$

where $$A_{1122}(\lambda_1, \lambda_2, \lambda_3) = \frac{(\lambda_1 + \lambda_2 + \lambda_3)^2}{18(\lambda_1 - \lambda_2)^2} \qquad [14]$$
$$\left[ \frac{\lambda_1 + \lambda_2}{\sqrt{\lambda_1 \lambda_2}} R_F\left(\frac{\lambda_3}{\lambda_1}, \frac{\lambda_3}{\lambda_2}, 1\right) + \frac{2\lambda_3 - \lambda_1 - \lambda_2}{3\sqrt{\lambda_1 \lambda_2}} R_D\left(\frac{\lambda_3}{\lambda_1}, \frac{\lambda_3}{\lambda_2}, 1\right) - 2 \right]$$

and $$A_{3333}(\lambda_1, \lambda_2, \lambda_3) = \frac{(\lambda_1 + \lambda_2 + \lambda_3)^2}{18(\lambda_3 - \lambda_1)(\lambda_3 - \lambda_2)} \left[ \frac{\sqrt{\lambda_1 \lambda_2}}{\lambda_3} R_F\left(\frac{\lambda_3}{\lambda_1}, \frac{\lambda_3}{\lambda_2}, 1\right) + \qquad [15] \right.$$
$$\left. \frac{3\lambda_3^2 - \lambda_1 \lambda_2 - \lambda_1 \lambda_3 - \lambda_2 \lambda_3}{3\lambda_3 \sqrt{\lambda_1 \lambda_2}} R_D\left(\frac{\lambda_3}{\lambda_1}, \frac{\lambda_3}{\lambda_2}, 1\right) - 1 \right].$$

with $R_F$ and $R_D$ being Carlson's elliptic integrals. Since there are highly efficient numerical algorithms for calculating Carlson's elliptic integrals, exemplary Equations [14] and [15] facilitate fast determination of the MK.

When $\lambda_1 = \lambda_2$, exemplary Equation [14] has a removable singularity. This can be resolved with:

$$A_{1122}(\lambda_1, \lambda_1, \lambda_3) = \qquad [16]$$

$$\frac{(2\lambda_1 + \lambda_3)^2}{144\lambda_1^2(\lambda_3 - \lambda_1)^2}\left[\lambda_1(2\lambda_1 + \lambda_3) + \lambda_3(\lambda_3 - 4\lambda_1)\alpha\left(1 - \frac{\lambda_3}{\lambda_1}\right)\right]$$

where $$\alpha(x) \equiv \begin{cases} \frac{1}{\sqrt{x}}\operatorname{arctanh}(\sqrt{x}), & \text{if } x > 0, \\ \frac{1}{\sqrt{-x}}\arctan(\sqrt{-x}), & \text{if } x < 0. \end{cases} \qquad [17]$$

When $\lambda_1 = \lambda_3$ or $\lambda_2 = \lambda_3$, exemplary Equation [15] has a removable singularity, which can be resolved with:

$$A_{3333}(\lambda_1,\lambda_2,\lambda_1) = 3A_{1122}(\lambda_1,\lambda_1,\lambda_2); A_{3333}(\lambda_1,\lambda_2,\lambda_2) = 3A_{1122}(\lambda_2,\lambda_2,\lambda_1) \qquad [18]$$

Further, for the special case when $\lambda_1 = \lambda_2 = \lambda_3$:

$$A_{1122} = \tfrac{1}{15}; A_{3333} = \tfrac{1}{5} \qquad [19]$$

Similarly, it is possible to determine the axial kurtosis from:

$$K_{\parallel} = \frac{(\lambda_1 + \lambda_2 + \lambda_3)^2}{9\lambda_3^2}\tilde{W}_{3333}, \qquad [20]$$

and the radial kurtosis from:

$$K_{\perp} = 6C_{1122}(\lambda_1,\lambda_2,\lambda_3)\tilde{W}_{1122} + \qquad [21]$$
$$C_{1111}(\lambda_1,\lambda_2,\lambda_3)\tilde{W}_{1111} + C_{1111}(\lambda_2,\lambda_1,\lambda_3)\tilde{W}_{2222},$$

where $$C_{1111}(\lambda_1,\lambda_2,\lambda_3) = \frac{(\lambda_1+\lambda_2+\lambda_3)^2}{18\lambda_1(\lambda_1-\lambda_2)^2}\left(2\lambda_1 + \frac{\lambda_2^2 - 3\lambda_1\lambda_2}{\sqrt{\lambda_1\lambda_2}}\right), \qquad [22]$$

and $$C_{1122}(\lambda_1,\lambda_2,\lambda_3) = \frac{(\lambda_1+\lambda_2+\lambda_3)^2}{18(\lambda_1-\lambda_2)^2}\left(\frac{\lambda_1+\lambda_2}{\sqrt{\lambda_1\lambda_2}} - 2\right). \qquad [23]$$

For the special case of $\lambda_1 = \lambda_2$, these determinations can reduce to:

$$C_{1111}(\lambda_1,\lambda_1,\lambda_3) = \frac{(2\lambda_1+\lambda_3)^2}{24\lambda_1^2}, \qquad [24]$$

and $$C_{1122}(\lambda_1,\lambda_1,\lambda_3) = \frac{(2\lambda_1+\lambda_3)^2}{72\lambda_1^2}. \qquad [25]$$

exemplary Equations [10]-[12] can be standard results used in diffusional tensor imaging data processing. However, exemplary Equations [13]-[25] can be important for real-time DKI data processing.

Exemplary Orientation Distribution Function(s)

One exemplary advantage of the orientation distribution function (ODF) for diffusion displacement probability distribution is that it can resolve fiber crossings in a model independent manner. A mathematical relationship between the ODF and the DK can demonstrate the ability of the DK-ODF to resolve fiber crossings by using simulations. In addition, an exemplary application of the DK-ODF to the brain is provided by exemplary examples of DK-ODF's calculated from human imaging data.

Exemplary Diffusional Kurtosis Approximation of Orientation Distribution Function(s)

Exemplary diffusional kurtosis imaging procedures can extend the Gaussian approximation of the diffusion distribution function by considering non-Gaussian contributions through an additional kurtosis term. For a direction specified by the unit vector n, the diffusion signal can be written as:

$$\ln[S(b)] = \qquad [26]$$
$$\ln[S(0)] - b\sum_{i=1}^{3}\sum_{j=1}^{3} n_i n_j D_{ij} + \frac{1}{6}b^2\bar{D}^2 \sum_{i=1}^{3}\sum_{j=1}^{3}\sum_{k=1}^{3}\sum_{l=1}^{3} n_i n_j n_k n_l W_{ijkl}$$

where $D_{ij}$ are the elements of the second order diffusion tensor D, and $W_{ijkl}$ the elements of the forth order kurtosis tensor W. D can represent the mean diffusivity $\bar{D} = \operatorname{Trace}(D)/3$. The exemplary diffusion and kurtosis coefficients along the n direction can be related to the respective tensors by the following equations:

$$D(\hat{n}) = \hat{n}^T \cdot D \cdot \hat{n} = \sum_{i=1}^{3}\sum_{j=1}^{3} \hat{n}_i \hat{n}_j D_{ij} \qquad [27a]$$

$$K(\hat{n}) = \frac{\bar{D}^2}{D(\hat{n})^2} \cdot \sum_{i=1}^{3}\sum_{j=1}^{3}\sum_{k=1}^{3}\sum_{l=1}^{3} \hat{n}_i \hat{n}_j \hat{n}_k \hat{n}_l W_{ijkl} \qquad [27b]$$

Both $D_{ij}$ and $W_{ijkl}$ can be symmetric with respect to an interchange of indices; consequently, D can have 6 independent degrees of freedom, and W can have 15 independent degrees of freedom. exemplary Equation [26] can be rewritten in terms of D(n) and K(n) as:

$$\ln[S(b)] = \ln[S(0)] - bD(\hat{n}) + \tfrac{1}{6}b^2 D(\hat{n})^2 K(\hat{n}) \qquad [28]$$

If P(s, t) represents the water diffusion displacement probability distribution for a displacement s and a diffusion time t, the ODF can be defined as its radial projection:

$$\psi(\hat{n}) = \frac{1}{Z}\int_0^{\infty} ds\, P(s\hat{n}, t) \qquad [29]$$

where Z is a normalization constant. An exemplary result of the DK-ODF approximation can be provided by:

$$\psi(\hat{n}) \approx \psi_{DK}(\hat{n}) \equiv \frac{1}{48\pi^2 Zt}\int d^3u \frac{3 + K(u)}{D(u)} \cdot \delta(\hat{n} \cdot u) \cdot \delta(|u|-1), \qquad [30]$$

with $\delta$ indicating the Dirac delta function. Because of the exemplary delta functions, the exemplary integral in exemplary Equation [30] can be one-dimensional and corresponds to a Funk transform, which can reduce the determination of the ODF value along a direction n to an integration of the signal values on a perpendicularly oriented great circle.

When n coincides with a coordinate axis 1, exemplary Equation [30] takes the form:

$$\psi(\hat{z}) \approx \psi_{DK}(\hat{z}) = \frac{1}{48\pi^2 Z t} \int_0^{2\pi} d\psi \frac{3 + K(\theta, \varphi)}{D(\theta, \varphi)}\bigg|_{\theta=\pi/2}, \quad [31]$$

where θ is the polar angle and φ is the azimuthal angle with respect to z. Thus, an exemplary approximation for the ODF in a particular direction can be obtained by integrating a function depending on the diffusion and kurtosis coefficients over the perpendicularly oriented great circle. The exemplary DK-ODF can facilitate the resolution of fiber crossings. Since a standard DKI data set can provide estimates for both the diffusion tensor and the kurtosis tensor, it is possible to use exemplary Equation [31] to also determine an approximate ODF. For example, $D(\theta, \varphi)$ and $K(\theta, \varphi)$ under the integrand can be approximated at any location on the great circle from the diffusion and kurtosis tensors using exemplary Equations [27a] and [27b].

In the DK approximation (e.g., exemplary Equation [31]), the ODF can be represented as a sum of two terms as follows:

$$\psi(\hat{z}) \approx \psi_{DK}(\hat{z}) = \quad [32]$$
$$\frac{1}{48\pi^2 Z t} \int_0^{2\pi} d\varphi \frac{3}{D(\theta, \varphi)}\bigg|_{\theta=\pi/2} + \frac{1}{48\pi^2 Z t} \int_0^{2\pi} d\varphi \frac{K(\theta, \varphi)}{D(\theta, \varphi)}\bigg|_{\theta=\pi/2}$$

where the first term corresponds to the Gaussian diffusion contributions and the second to the non-Gaussian diffusion contributions. These exemplary diffusion contribution can be referred to as the Gaussian and non-Gaussian (NG) DK estimated ODFs, respectively. The total ODF can then be written as:

$$\psi_{DK}(\hat{n}) = \psi_{G-DK}(\hat{n}) + \psi_{NG-DK}(\hat{n}) \quad [33]$$

Exemplary ODF for Gaussian Diffusion Approximation Procedure(s)

For Gaussian diffusion, the displacement probability distribution can have the form of:

$$P(s, t) = \frac{1}{(4\pi t)^{3/2}|D|^{1/2}} \cdot \exp[-s^T \cdot D^{-1} \cdot s / 4t] \quad [34]$$

For this exemplary embodiment, it can be verified that K=0 and that:

$$\psi(\hat{n}) = \psi_{DT}(\hat{n}) = \frac{1}{8\pi Z t|D|^{1/2}} \cdot \left(\frac{1}{\hat{n}^T \cdot D^{-1} \cdot \hat{n}}\right)^{1/2} \quad [35]$$

An exemplary disadvantage of the DT-ODF is that it may not allow fiber crossings to be resolved.

More generally, $\psi_{DT}$ can be regarded as a "diffusion tensor approximation" for the ODF. Exemplary Equation [35] can be used to fix the normalizations of the ODF approximations by setting:

$$Z = \frac{1}{8\pi \overline{D} t} \quad [36]$$

so that the ODF is dimensionless and equal to unity for isotropic Gaussian diffusion.

Exemplary Simulations

To test the DK-ODF, a multi-compartment exemplary model can be utilized with the displacement probability distributions of the form of:

$$P(s, t) = \sum_{m=1}^{N} f_m \frac{1}{(4\pi t)^{3/2}|D^{(m)}|^{1/2}} \cdot \exp\{-s^T \cdot [D^{(m)}]^{-1} \cdot s / 4t\}, \quad [37]$$

where N is the number of compartments, $D^{(m)}$ the diffusion tensor for the mth compartment, and $f_m$ its corresponding water fraction with the water fractions $f_m$ adding to unity $$\sum_{m=1}^{N} f_m = 1.$$

For example, the exact ODF for this model can be given by:

$$\psi(\hat{n}) = \sum_{m=1}^{N} \frac{f_m}{8\pi Z t|D^{(m)}|^{1/2}} \cdot \left\{\frac{1}{\hat{n}^T \cdot [D^{(m)}]^{-1} \cdot \hat{n}}\right\}^{1/2}. \quad [38]$$

The exemplary diffusion and kurtosis tensors can be obtained as combinations of the diffusion tensors describing the individual compartments:

$$D = \sum_{m=1}^{N} f_m D^{(m)}, \quad [39]$$

$$W_{ijkl} = \frac{1}{\overline{D}^2} \left\{ \sum_{m=1}^{N} f_m [D_{ij}^{(m)} D_{kl}^{(m)} + D_{ik}^{(m)} D_{jl}^{(m)} + D_{il}^{(m)} D_{jk}^{(m)}] - D_{ij} D_{kl} - D_{ik} D_{jl} - D_{il} D_{jk} \right\}. \quad [40]$$

The ODF-DK can be estimated using exemplary Equation [32], where D(n) and K(n) values can be obtained from the diffusion and kurtosis tensor, respectively.

Exemplary mixed fiber models having two to four compartments were used. For all the models, the eigenvalues of $D^{(m)}$ were chosen to be 0.3, 0.3, and 1.8 μm²/ms, so that the diffusion within each compartment was highly anisotropic (fractional anisotropy=0.81). Mixtures with different weights were investigated. For each model, the exact and DK and QB estimated ODFs were calculated and displayed, as well as the exact and DK estimated non-Gaussian ODFs (NG-ODF). A b value of 4000 s/mm² was assumed for calculating the QB-ODF as an approximate and typical value. For comparison purposes, the Gaussian (DT) ODF was also calculated for each model.

Exemplary Diffusional Restrictivity

An exemplary diffusional restrictivity at a time t can is defined as:

$$R_D(t) = 2t \left\langle \frac{1}{[r(t) - r(0)] \cdot [r(t) - r(0)]} \right\rangle. \quad [41]$$

where r(t) can be a diffusion path and the angle brackets indicate an averaging over a region of interest. The restrictivity may be calculated from the orientation distribution function using the equation:

$$R_D = 2Zt \int d^3 u \psi(u) \delta(|u|+1). \quad [42]$$

From this, the approximate expression can be derived:

$$R_D \approx \frac{1}{12\pi} \int d^3 u \frac{3 + K(u)}{D(u)} \delta(|u| - 1). \quad [43]$$

Since both D(u) and K(u) can be obtained with DKI, this shows how DKI can be used to estimate the diffusional restrictivity.

Exemplary MRI Experiment

Exemplary imaging experiments were conducted on a 3 T Trio M R system (Siemens Medical Solutions, Erlangen, Germany) using a body coil for transmission and an eight-element phase array coil for reception. Exemplary DKI data was obtained for six healthy volunteers using a predetermined protocol. Diffusion weighted images were acquired for 30 uniformly distributed gradient directions and for five b-values (500, 1000, 1500, 2000 and 2500 s/mm$^2$) using a twice refocused-spin-echo EPI sequence, which has been shown to significantly reduce the eddy-current-related distortions in the diffusion weighted images. In addition, data without any diffusion weighting (b=0 s/mm) was obtained. Other imaging parameters included: TR=2000 ms, TE=109 ms, FOV=256×256 mm$^2$, matrix=128×128, a parallel imaging factor of 2, number of images averaged (NEX)=2, 6/8 partial Fourier in phase-encoding direction, 15 axial slices, with a slice thickness of 2 (acquisition 1) or 4 mm (acquisition 2) and gap of 2 mm. The total duration for acquiring a DKI data set was 12 minutes.

Exemplary Image Data Processing Procedure(s)

The diffusion weighted images were first corrected for motion and spatially smoothed using SPM using a two-dimensional Gaussian filter with FWHM of 2.5 mm. The diffusion and kurtosis tensors were subsequently calculated. Only those data points that exceeded the value representing the 90th percentile of the noise range were included in the calculation, where noise values were sampled using a 10×10×13 volume situated outside a brain. The tensor calculation included: a) estimation of the apparent diffusivity and kurtosis values along each of the thirty encoding directions using Levenberg-Marquardt nonlinear fitting procedure for exemplary Equation [28], b) diffusion tensor estimation from a set of apparent diffusivities, and c) kurtosis tensor estimation (using exemplary Equation [27b]) using the apparent kurtosis values estimated at procedure (a) and the set of corrected apparent diffusion values obtained using the diffusion tensor estimated at procedure (b).

The exemplary diffusion tensor eigenvectors and eigenvalues, and the fractional anisotropy were calculated and used to obtain directional color maps and to depict the fiber direction estimates using a Gaussian approximation. The exemplary color maps were used for anatomical reference.

The non-Gaussian (NG), Gaussian, and total ODFs were calculated at each voxel using exemplary Equation [32] on a grid of 60×60 data points (corresponding to equally spaced θ and φ values). For each grid point, the ODF value was estimated by integrating along the equator circle perpendicular to a grid point direction, and the D(n) and K(n) values in the integrand were obtained from the diffusion and kurtosis tensors, respectively. In order to better distinguish visually the directional variations in the ODF profile, a 0 to 1 resealed min-max version of the non-Gaussian ODF was also calculated (i.e., the minimum ODF value is scaled to 0 and the maximum ODF value is scaled to 1). The exemplary fiber directions at each voxel were determined from the ODF peaks. The ODF surfaces were superimposed onto mean kurtosis maps and were color-coded using the typical mapping of the x, y, and z spatial directions to a red, green, and blue color triad.

Exemplary Simulations

FIGS. 1(a)-1(f) illustrate exemplary three-dimensional ODF surfaces for diffusion models including two (top row) and three (bottom row) equally contributing fibers (i.e., $f_m=1/N$) intersecting at a high angle (>80°). For example, FIG. 1(a) illustrates an exemplary exact ODF, FIG. 1(b) illustrates an exemplary DK estimation of the ODF, FIG. 1(c) illustrates an exemplary exact NG-ODF, FIG. 1(d) illustrates an exemplary DK estimation of the NG-ODF, FIG. 1(e) illustrates an exemplary q-ball estimation of the ODF (min-max scaled) for a b-value of 4000 s/mm$^2$, and FIG. 1(f) illustrates an exemplary Gaussian estimation of the ODF. The directions of the exemplary component fibers are shown in these figures by the dashed lines, and the fiber orientations are $(\theta_1, \varphi_1)=(50°, 90°)$ and $(\theta_2, \varphi_2)=(130°, 90°)$ for N=2 and $(\theta_1, \varphi_1)=(60°, 90°)$, $(\theta_2, \varphi_2)=(120°, 40°)$, (03, 603)=(120°, 130°) for N=3. An appropriate correspondence can be seen between the direction of the fibers (indicated by dashed lines) and the ODF peaks for both the DK and QB approximations, with no offset between the true and the estimated directions. The NG-ODF gives a good peak delineation.

In FIGS. 2(a)-2(f), exemplary images of exemplary three dimensional surfaces of the exact and estimated ODF are illustrated for diffusion models with two fibers with volume fractions of 30% and 70% (top row) and two equally contributing fibers intersecting at an angle of 30° (bottom row). For example, FIG. 2(a) illustrates an exemplary exact ODF, FIG. 2(b) illustrates an exemplary DK estimation of the ODF, FIG. 2(c) illustrates an exemplary exact NG-ODF, FIG. 2(d) illustrates an exemplary DK estimation of the NG-ODF, FIG. 2(e) illustrates an exemplary q-ball estimation of the ODF (min-max scaled) for a b value of 4000 s/mm$^2$, and FIG. 2(f) illustrates an exemplary Gaussian estimation of the ODF. The directions of the exemplary component fibers are shown by dashed lines. The fiber orientations shown in FIG. 2(a) are the same as those in FIG. 1(a). The fiber orientations shown in FIG. 2(b) are: (θ1, φ1)=(50°, 90°) and (θ2, φ2)=(80°, 90°).

Individual fibers can be resolved in cases where one compartment has a greater contribution than the other one, as illustrated in FIG. 2(a). An appropriate approximation of the component fiber orientations can be observed for a small angle of intersection in FIG. 2(b), (angle of intersection=30°) for the DK-ODF, though the ODF peaks were offset with respect to the chosen fiber direction by approximately 8°. The two fiber components are no longer apparent with the QB-ODF approximation (see FIG. 2(e)). These exemplary simulations indicate that DK-ODF is capable of resolving fiber crossing at angles as small as 2° for two fiber configurations—however the offset to the true orientation in this case reached 18°. The offset decreases as the angle of separation increases. As the number of fiber directions increases, the DK-ODF approximation appears to resolve orthogonal or close to orthogonal fiber configurations, as illustrated in FIG. 1(b). Offsets of the exemplary ODF peaks with respect to the component fiber directions are also apparent at small intersection angles for the exact ODF.

Exemplary Brain Imaging Experiments

An exemplary DK approximation was used to derive ODF maps of the in vivo brain imaging data. Similar results were obtained for all subjects. FIGS. 3-5 show the absolute and min-max normalized DK-derived NG-ODF maps and the corresponding DT-ODF maps for several brain regions where complex fiber architecture is present. Voxels with multiple fiber components can be distinguished on the DK-ODF maps. In general, the min-max normalization can improve the visualization of the ODF peaks. The fiber orientations resolved using the DK approximation are consistent with known anatomy. Complex fiber architecture is not apparent on the DT-ODF maps.

Figure 3A:
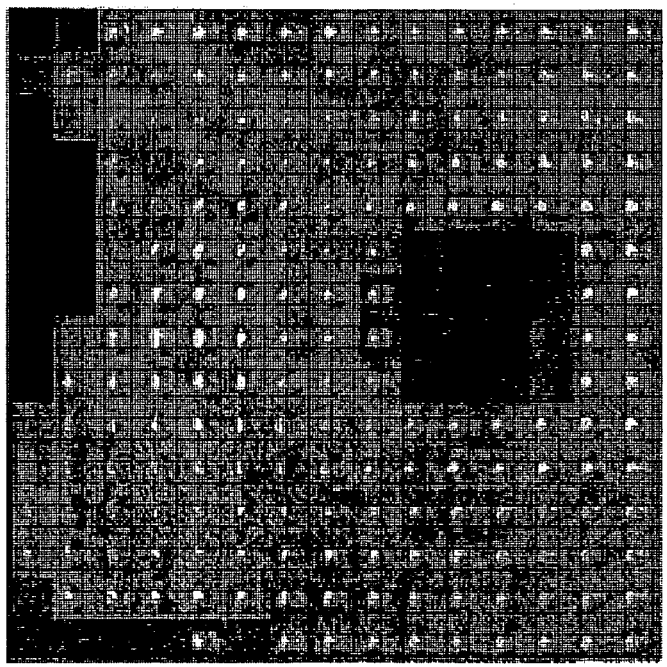
Figure 3D:
Figure 3E:
Figure 3C:
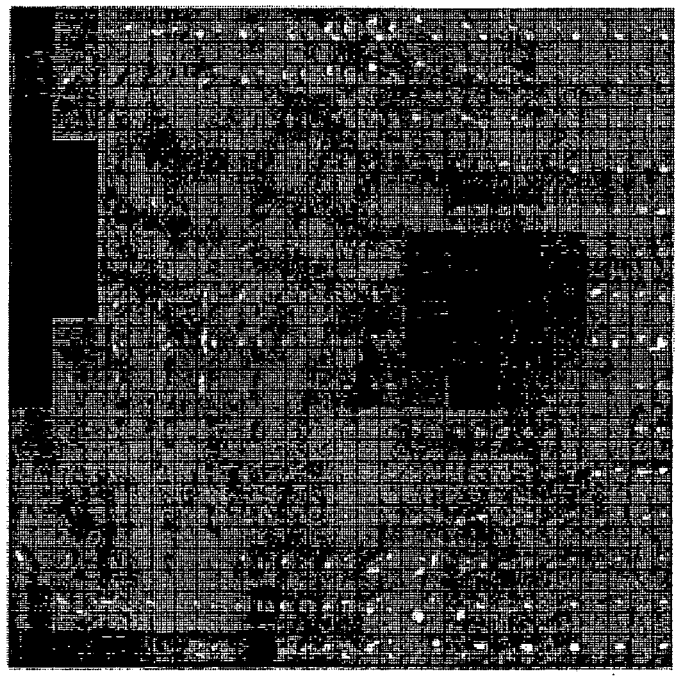

FIGS. 3(a)-3(e), 4(a)-4(e) and 5(a)-5(d) show exemplary ODF maps of an axial slice situated at the cerebral pons level. Such exemplary region contains several fiber populations including the superiorly—inferiorly oriented pyramidal and central tegmental tracts and the transverse pontine fibers that are running from left to right. For example, FIG. 3(a) illustrates an exemplary DT approximation, FIG. 3(b) illustrates an exemplary DK-derived NG-ODF, and FIG. 3(c) illustrates an exemplary min-max scaled version of FIG. 3(b). An exemplary DT derived color map of the same axial slice and location of the ODF maps are illustrated in FIG. 3(d). Fiber directions obtained using the DK (left-unsealed ODF and center—min-max scaled ODF) and DT (right) approximations for one voxel with apparent partial volume averaging of two fiber populations are illustrated, as an example, in FIG. 3(e).

Two fiber directions (transverse and superior-inferior) are shown in regions with mixed fiber populations (see FIGS. 3(b) and 3(c)); these fiber directions appear to be in agreement with known anatomy. The DT approximation does not only fail to resolve the two fiber populations in voxels affected by partial volume averaging, but appears to fail to describe either orientation correctly (e.g., see FIG. 3(e)).

Figure 4B:
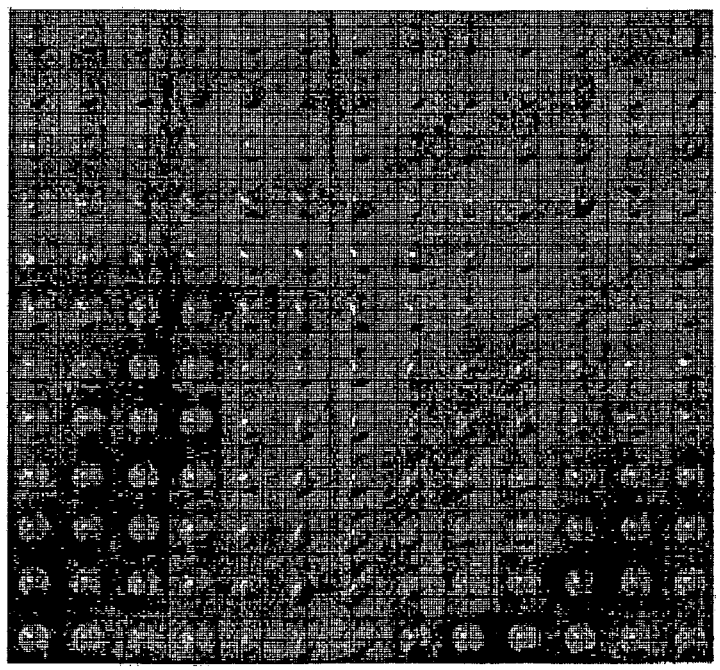
FIGS. 4(a)-4(e) are other illustrations of further exemplary ODF maps of the brainstem, in accordance with certain exemplary embodiments of the present disclosure.
Figure 4A:
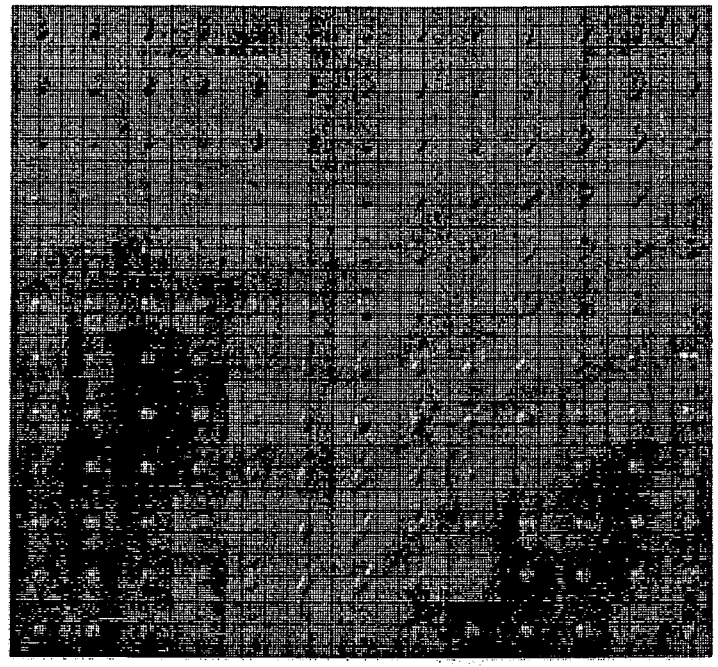
Figure 4D:
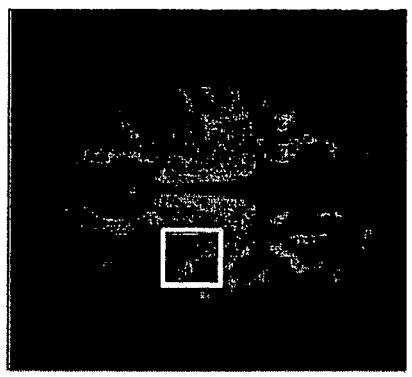
Figure 4E:
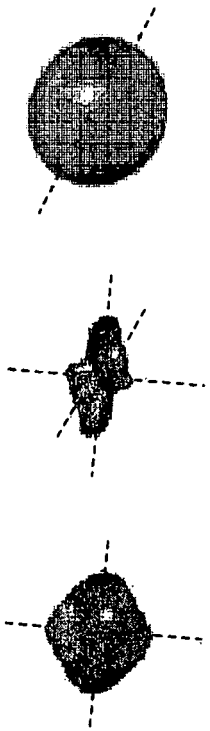
Figure 4C:
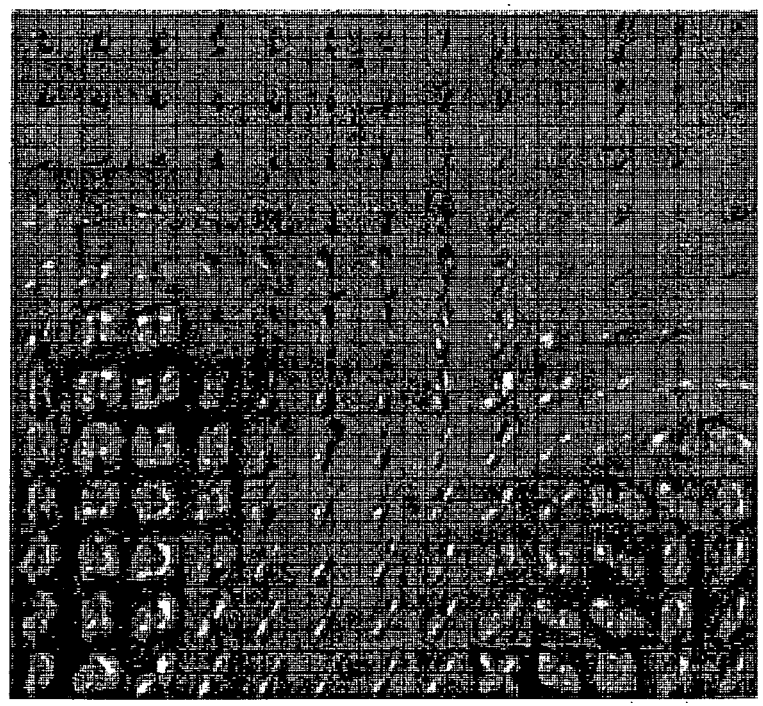

FIGS. 4(a)-4(e) show exemplary intersections of the superior longitudinal fasciculus (SLF), corona radiata, and corpus callosum in the centrum semiovale region. For example, FIG. 4(a) illustrates an exemplary DT approximation, FIG. 4(b) illustrates an exemplary DK-derived NG-ODF, and FIG. 4(c) illustrates an exemplary min-max scaled version of FIG. 4(b). An exemplary color map in FIG. 4(d) illustrates a position of the ODF maps with respect to other brain structures. FIG. 4(e) illustrates exemplary ODFs and corresponding fiber directions for a voxel where three distinct fiber populations are apparent using the DK approximation. Exemplary regions with two and three fiber populations are illustrated on the DK-ODF map. On the DK-ODF map, the SLF runs continuously in the anterior-posterior direction, whereas it is interrupted on the color map which was obtained using the exemplary DT-ODF approximation.

FIGS. 5(a)-5(d) illustrate exemplary ODF maps of the intersection between the posterior region of the superior longitudinal fasciculus with the projection fibers of the corona radiata and the posterior transverse association fibers for acquisition. For example, FIG. 5(a) illustrates an exemplary DT approximation, FIG. 5(b) illustrates an exemplary DK-derived NG-ODF (min-max scaled), FIG. 5(c) illustrates an exemplary DT-derived color map that shows the position of the magnified views with respect to other brain structures, and FIG. 5(d) illustrates exemplary fiber directions obtained using the DK (left-unsealed ODF and center min-max scaled ODF) and DT (right) approximations for several voxels. Voxels with two-fiber populations are also shown in the DK-ODF maps illustrating regions where the posterior SLF interfaces with either corona radiata or transverse association fibers running from left to right. The ODF shows changes in shape and orientation as it represents either mixtures of fibers running anteriorly-posteriorly and vertically oblique or mixtures of fibers oriented anteriorly-posteriorly and from right to left, as illustrated, as example, in FIGS. 5(b) and 5(c).

Exemplary Parametric Maps

FIGS. 6(a)-6(d) show exemplary brain images of a mean diffusivity, axial diffusivity, radial diffusivity and a fractional anisotropy, respectively, provided by conventional diffusion tensor imaging. The data can be obtained using a, e.g., magnetic resonance imaging scanner. For example, the mean diffusivity illustrated in FIG. 6(a) can be derived, e.g., using exemplary Equation [6]. The axial diffusivity illustrated in FIG. 6(b) can be derived, e.g., using exemplary Equation [10]. The radial diffusivity illustrated in FIG. 6(c) can be derived, e.g., using exemplary Equation [11], and the fractional anisotropy illustrated in FIG. 6(d) can be derived, e.g., using exemplary Equation [12]. The mean, axial, and radial diffusivities, provided in FIGS. 6(a)-6(c), respectively, and the fractional anisotropy provided in FIG. 6(d) are similar to what can be generated with conventional diffusion tensor imaging. Calibration bars shown in these figures are in units of $\mu m^2/ms$ for the mean, axial, and radial diffusivities, and calibration bars can be dimensionless for the fractional anisotropy.

FIGS. 7(a)-7(c) show images of exemplary parametric maps derived with real-time diffusional kurtosis imaging for a single axial brain slice using an exemplary embodiment of the present disclosure. The mean, axial, and radial kurtoses, as illustrated in FIGS. 7(a)-7(c), respectively, can be exemplary metrics provided by DKI. The mean kurtosis illustrated in FIG. 7(a) can be derived, e.g., using exemplary Equation [13]. The axial kurtosis illustrated in FIG. 7(b) can be derived, e.g., using exemplary Equation [20], and the radial kurtosis illustrated in FIG. 7(c) can be derived, e.g., using exemplary Equation [21]. Calibration bars can be dimensionless for the mean, axial, and radial kurtoses illustrated in FIGS. 7(a)-7(c), respectively.

Further Details of Exemplary Embodiments

An exemplary ODF reconstruction procedure based on the DK approximation of the diffusion signal is described herein. The fiber crossing simulation results support the ability of the DK-ODF approximation to resolve multiple volume averaged fibers. The technique can estimate the directionality for mixtures of two, three or four intersecting fibers. The offset between the true and the estimated fiber directions that is observed for fibers intersecting at a small angle is characteristic to other HARDI techniques and is provided by the ODF model. This can be due to adherence between the closely situated peaks on the ODF.

The exemplary simulations included use analytical representations of the diffusion probability distribution function and the ODFs, and may not model the influence of the imaging acquisition scheme and signal-to-noise ratio.

The DK-ODF maps of the brain anatomy can correspond to the current knowledge of white matter fiber architecture. Configurations with both two and three crossing fibers as well as unidirectional voxels are all apparent on the ODF maps.

One of the exemplary advantages of DKI is that can use low b values (b<2500 s/mm2) This can result in diffusion-weighted images with relatively higher signal to noise ratio compared to the signal-to-noise ratio of images used by other ODF techniques. Moreover, the exemplary DK approximation can include only the lower moments of the water diffusion distribution (up to the forth order), thus retaining only the low frequency components of the ODF spherical harmonic spectrum. Additional smoothing may be also introduced by the linearization of the signal in the kurtosis coefficient K that is used to derive the ODF approximation and by using the diffusion and kurtosis tensors to estimate the diffusion and kurtosis coefficients used in the Funk-Radon transform. Consequently, the reconstructed ODFs can be inherently smooth, and do not require further regularization (e.g., spherical convolution), which is usually employed by other ODF techniques. Further, the exemplary derivation of the diffusion and kurtosis tensor employed by DK-ODF can use a limited number of measurements.

An alternative exemplary approach for obtaining directional information in regions with complex fiber architecture is to use q-space imaging (QSI) techniques to extract the full diffusion displacement probability distribution. However, the QSI techniques require a large number of samples and high b values, thus resulting in long imaging times and images with low signal to noise ratio. Further, the DK-ODF model, in contrast with the QBI-ODF approximations, has no explicit b-value dependence.

Figure 8:
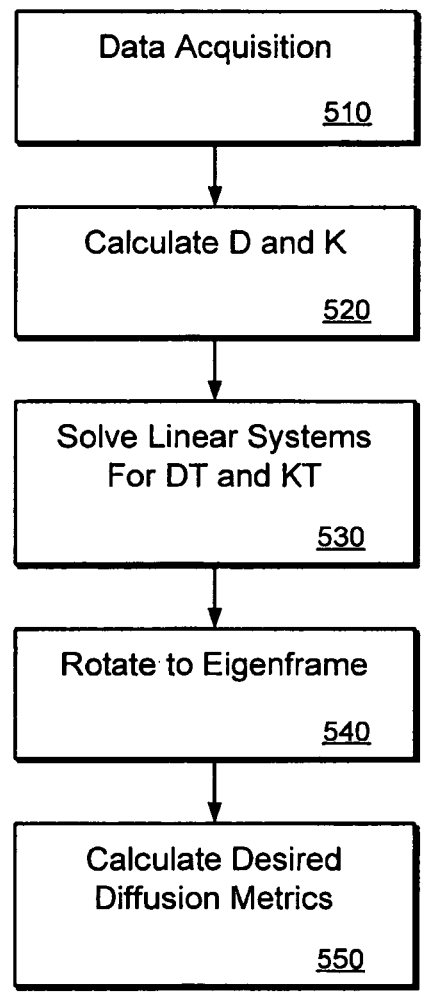
FIG. 8 is a flow diagram according to an exemplary embodiment of a method of an exemplary real-time diffusional kurtosis imaging, in accordance with certain exemplary embodiments of the present disclosure.

Further Exemplary Embodiments of Methods, Systems and Computer-Accessible Medium FIG. 8 illustrates a flow diagram according to an exemplary embodiment of a method of an exemplary real-time diffusional kurtosis imaging according to the present disclosure. For example, in 510, data can be acquired, e.g., using a diffusion-weighted imaging MRI sequence with 3 b-values and 15 or more diffusion directions. At 520, the diffusion D and kurtosis K can be calculated for each diffusion direction. Such calculation can be provided, e.g., using the analytic formulae of exemplary Equations [1]-[3]. At 530, linear systems, as exemplified by exemplary Equations [4] and [5], can be solved for the diffusion tensor DT and kurtosis tensor KT. At 540, the method can rotate to eigenframes that diagonalizes the diffusion tensor, by applying any of several exemplary standard techniques, such as Jacobi's method. Further, at 550, analytic formulae or procedures can be used to calculate the desired diffusion metrics, such as mean, axial and radial diffusivities and mean, axial and radial kurtoses. The mean, axial, and radial diffusivities can be derived using exemplary Equations [6], [10], and [11]. The mean, axial, and radial kurtoses can be derived using exemplary Equations [13], [20], and [21]. Such diffusion metrics can provide for real-time diffusional kurtosis imaging.

Figure 9:
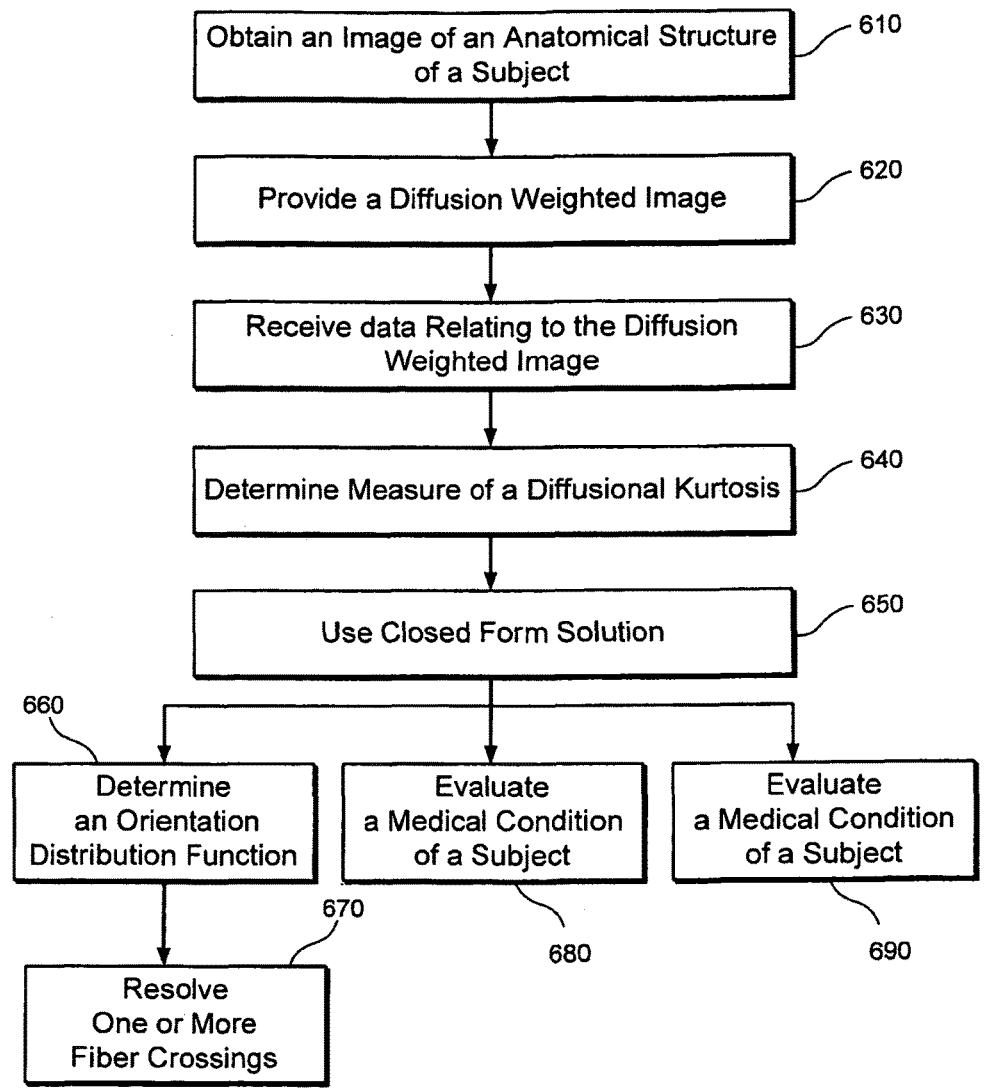
FIG. 9 is a flow diagram according to an exemplary embodiment of a method according to certain exemplary embodiments of the present disclosure.

FIG. 9 illustrates a flow diagram of an exemplary method for determining a measure of a diffusional kurtosis according to an exemplary embodiment of the present disclosure. Initially, e.g., at procedure 610, an image can be obtained of an anatomical structure, such as a portion of a brain of a subject, such as a human subject. This exemplary image can be provided by several different methods or procedures, such as, e.g., by MRI. A diffusion weighted image of the image can be provided at procedure 620. The diffusion weighted image can be acquired for three or more b-values, and can be acquired for 15 or more gradient directions. Data can then be received relating to the diffusion weighted image at procedure 630.

At procedure 640, a measure of a diffusional kurtosis can be determined. This diffusional kurtosis can be measured using a closed form solution at procedure 650, as described above. The measure of the diffusional kurtosis can be determined using a mean kurtosis as well, which can be determined by averaging measures of a diffusion and a kurtosis over each gradient direction. The measure of the diffusional kurtosis can also be an axial kurtosis or a radial kurtosis.

Using the measure of the diffusional kurtosis, an orientation distribution function can be determined at procedure 660. One or more fiber crossings can be resolved using the orientation distribution function at procedure 670. The fiber crossing can be a crossing of two, three or four fibers, or more. Further, a medical condition of the subject can be evaluated using the measure of the diffusional kurtosis at procedure 680, such as Alzheimer's disease, stroke, head trauma, attention deficit hyperactivity disorder or schizophrenia. A measure of diffusional restrictivity can also be determined using the measure of the diffusional kurtosis, at procedure 690.

Figure 10:
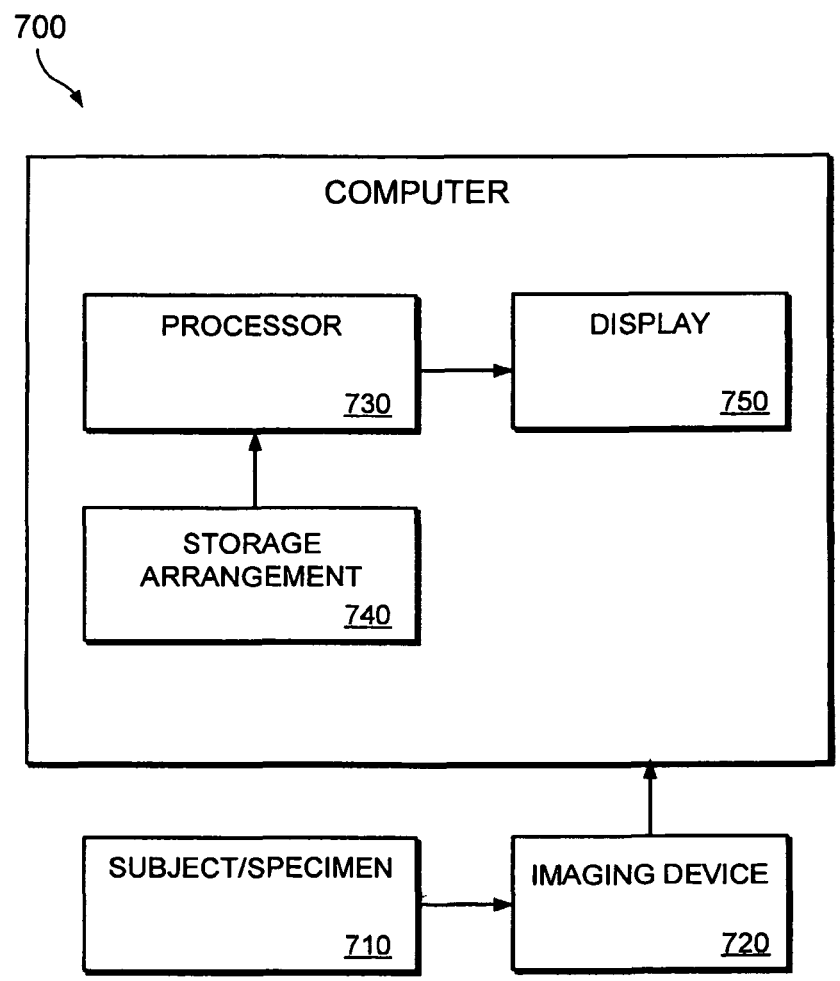
FIG. 10 is a block diagram of an exemplary embodiment of a system according to certain exemplary embodiments of the present disclosure.

FIG. 10 illustrates a block diagram of an exemplary embodiment of a system according to the present disclosure. For example, a computer 700 can be provided which can have a processor 730 that can be configured or programmed to perform the exemplary steps and/or procedures of the exemplary embodiments of the techniques described above, and those as described herein with respect to the exemplary procedure shown in FIG. 9. For example, a subject/specimen 710 can be positioned and an anatomical region of interest can be selected on the subject/specimen 710, as provided for in procedure 610 above. The imaging device 720 can be used to obtain data for one or more images of the anatomical region of interest. The data/images (e.g., diffusion weighted images) can be provided from the imaging device 720 to the computer 700, which can be transmitted to the processor 730 and/or storage arrangement 740.

According to one exemplary embodiment of the present disclosure, the data can be stored in a storage arrangement 740 (e.g., computer-accessible medium, hard drive, memory device, such as RAM, ROM, memory stick, floppy drive, etc.). The processor 730 can access the storage arrangement 740 to execute a computer program or a set of instructions (stored on or in the storage arrangement 740) which perform the procedures according to the exemplary embodiments of the present invention. Thus, e.g., when the processor 730 performs such instructions and/or computer program, the processor 730 can be configured to perform the exemplary embodiments of the procedures according to the present invention, as described above herein.

For example, the processor 730 can be programmed to receive data relating to at least one diffusion weighted image, and determine a measure of a diffusional kurtosis as a function of the received data. This information can be received directly from the imaging device 720 or accessed from the storage arrangement 740. The processor 730 can also be programmed to determine information for measuring a diffusional kurtosis, and can then resolve one or more fiber crossings, evaluate a medical condition of the subject, and/or measure a diffusion restrictivity.

A display 750 can also be provided for the exemplary system of FIG. 7. The storage arrangement 740 and the display 750 can be provided within the computer 700 or external from the computer 700. For example, the information received by the processor 730 and the information determined by the processor 730, as well as the information stored on the storage arrangement 740 can be displayed on the display 750 in a user-readable format.

Exemplary Estimation of Tensors and Tensor-Derived Measures in DKI

According to exemplary embodiments of the present disclosure, it is possible to estimate tensors and tensor-derived measures in DKI. For example, for direction vector g and b-value b, the diffusion signal intensity S(g,b) can be written as, e.g., $$\ln S(g, b) = \ln S_0 - b \sum_{i=1}^{3}\sum_{j=1}^{3} g_i g_j D_{ij} + \frac{1}{6} b^2 \overline{D}^2 \sum_{i=1}^{3}\sum_{j=1}^{3}\sum_{k=1}^{3}\sum_{l=1}^{3} g_i g_j g_k g_l W_{ijkl} \quad [44]$$

Where $S_0$ can represent the signal intensity for b=0, $D_{ij}$ and $W_{ijkl}$ can represent the elements of the second-order diffusion tensor D and fourth-order kurtosis tensor W, respectively, and $\overline{D}=(\frac{1}{3})$ tr(D) can represent mean diffusivity, where tr(.) can denote matrix trace. Diffusivity and kurtosis along direction g, which can be denoted as D(g) and K(g), respectively, can be provided by, e.g., $$D(g) = \sum_{i=1}^{3}\sum_{j=1}^{3} g_i g_j D_{ij} \quad [45]$$

and $$K(g) = \frac{\overline{D}^2}{D(g)^2} \sum_{i=1}^{3}\sum_{j=1}^{3}\sum_{k=1}^{3}\sum_{l=1}^{3} g_i g_j g_k g_l W_{ijkl}$$

According to certain exemplary embodiments of the present disclosure, to ensure that the diffusivity and kurtosis parameters can be physically and biologically plausible, the following can be had:

$$D(g) \geq 0 \text{ and } K_{max}(g) \geq k(g) \geq K_{min}, \text{ for all } g$$

where $K_{min}$ can represent a constant in the [−2, 0] range, and $K_{max}(g)=C/[b. D(g)]$, where 3≥C≥0. The objective in the estimation problem can be to find D and W such that the mean-square error between the two sides of exemplary Equation [44] is minimized, while the constraints in exemplary Equation [46] are satisfied. For example, using the change of variable $V=\overline{D}^2 W$ and for a likely typical choice of $K_{min}=0$, the problem of estimating D and V can be formulated as a CLLS problem. For other $K_{min}$ values, the problem can be approximated using, e.g., CLLS. The CLLS problem can be a special case of convex quadratic programming which can be efficiently solved via certain known methods.

EXEMPLARY METHODS

An exemplary DKI scan according to certain exemplary embodiments of the present disclosure was performed on a healthy volunteer using a 3T Siemens Trio system with an 8-channel head coil. Exemplary diffusion-weighted images were acquired along 30 gradient directions with a twice-refocused spin-echo planar imaging sequence (TR=2300, TE=109 ms, matrix=128×128, FOV=256×256 mm², 15 slices, slice thickness=2 mm, gap=2 mm, NEX=6 for b=0, NEX=2 for b=1000, 2000 s/mm²). The gradient images were smoothed prior to processing using a Gaussian kernel with a full width at half maximum of 2.5 mm in the imaging plane. The active set method implemented in MATLAB was used to solve the CLLS problem. MK was also estimated using ULLS, where the constraints in exemplary Equation [46] were relaxed. Two processing scenarios were considered, as described as follows, for example: In one scenario, MK was obtained using all of the available gradient images.

In the other scenario, MK was estimated using 6 of b=1000 s/mm² and all of b=2000 s/mm² gradient images.

Exemplary Results

Figures 12A, 12B:
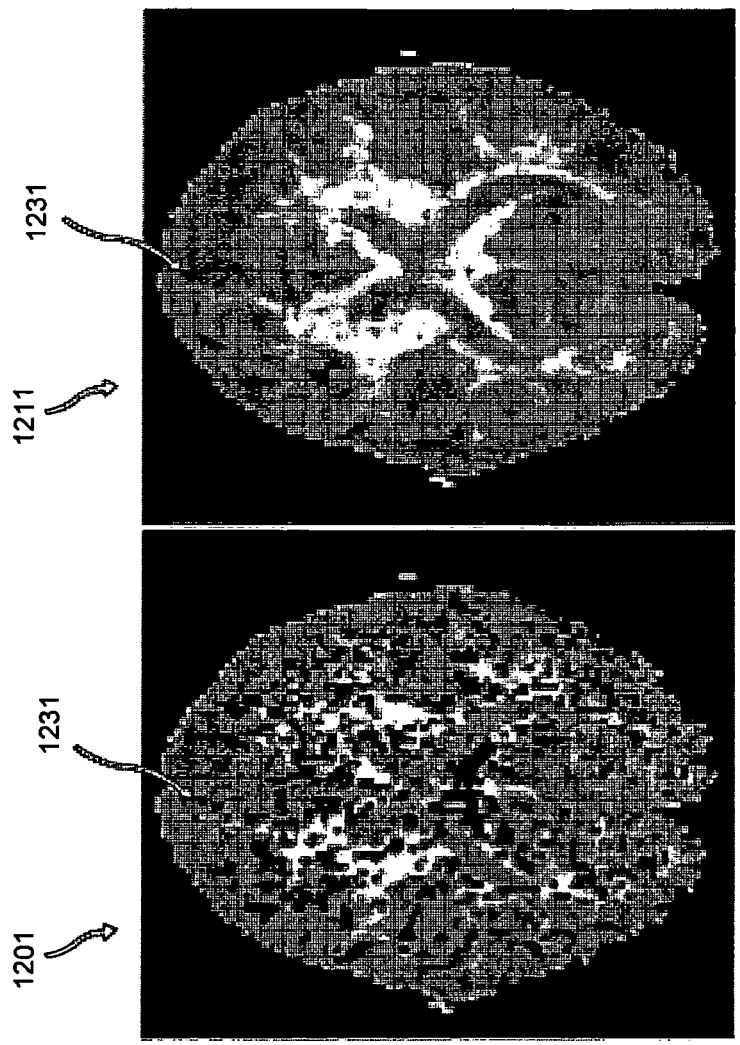
FIG. 12(a) is an illustration of another exemplary image map produced with ULLS, in accordance with certain exemplary embodiments of the present disclosure.
FIG. 12(b) is an illustration of still another exemplary image map generated using an exemplary embodiment of CLLS, in accordance with certain exemplary embodiments of the present disclosure.

The total processing time for generating scalar kurtosis and diffusion maps using all gradient images was 136 and 335 seconds for ULLS and CLLS, respectively. FIGS. 11(a), 11(b), 12(a) and 12(b) are exemplary illustrations that show the improved quality of the MK maps 1101, 1111, 1201, 1211 obtained using an exemplary embodiment of CLLS in accordance with the present disclosure over those estimated via an ULLS approach. As shown in FIGS. 11(a), 11(b), 12(a) and 12(b), voxels 1131, 1231 for which the ULLS approach yielded MK estimates smaller than $K_{min}=0$, where are marked in black. As shown in FIGS. 11(a) and 11(b), voxels 1131, 1231 can be most likely to occur in high FA regions such as parts of the corpus callosum, although, as shown in FIGS. 12(a) and 12(b), they can be scattered in other parts of white matter as well.

Exemplary Discussion

The exemplary voxels 1131, 1231 shown in FIGS. 11(a), 11(b), 12(a) and 12(b) where CLLS produces improved MK estimates can be those for which ULLS yields a nonpositive definite (NPD) and/or nearly NPD estimate of D. In these voxels, the smallest eigenvalue of D, which can be denoted as $\lambda_3$, can have a relatively small magnitude, which in turn can cause the ULLS estimate of D to be more sensitive to noise, for example. The constraints in exemplary Equation [46] can force a larger $\lambda_3$ yielding a more reasonable (e.g., preferred, accurate, etc.) estimate of D and W in these regions. Accordingly, exemplary embodiments of systems, computer-accessible medium, methods and/or procedures according to the present disclosure can utilize CLLS to provide an exemplary tractable means for, e.g., parameter estimation via minimizing a convex cost function, thus avoiding local minima and achieving reasonable (e.g., preferred, increased, etc.) speed.

Moreover, according to certain exemplary embodiments according to the present disclosure, it is possible to achieve improved noise robustness over unconstrained schemes/approaches by, e.g., providing, facilitating and/or ensuring that the estimated diffusivity and/or kurtosis remain within a physically and/or biologically plausible (e.g., acceptable, preferred, etc.) range along the imaged gradient directions. The examples described herein using actual image data highlight some of the advantages provided by exemplary embodiments according to the present disclosure over, e.g., the ULLS approach. For example, the improvement can be particularly evident with fewer b=1000 s/mm² acquisitions, as shown in FIGS. 12(a) and 122(b).

Another important exemplary advantage that can be provided by certain exemplary embodiments according to the present disclosure over a fast DKI estimation method can be that exemplary embodiments according to the present disclosure can accept any (or virtually any) number of b-values and/or different numbers of gradient directions per b-value, which can enable, e.g., further optimization of the acquisition protocol. For example, the comparable quality of the MK maps 1111 and 1211 illustrated in FIGS. 11(b) and 12(b), respectively, can suggest that to achieve a certain map quality, the exemplary embodiment of a CLLS procedure according to the present disclosure can involve fewer gradient images at b=1000 s/mm² as compared to ULLS, which, in this example, can provide a savings (e.g., reduction) of about 38% in acquisition time.

Further, it is possible to speed up exemplary computations and procedures according to the present disclosure via, e.g., parallelization, which can be used to address the potential increased algorithm complexity and consequently higher run time that can be associated with certain exemplary embodiments according to the present disclosure.

Figure 13:
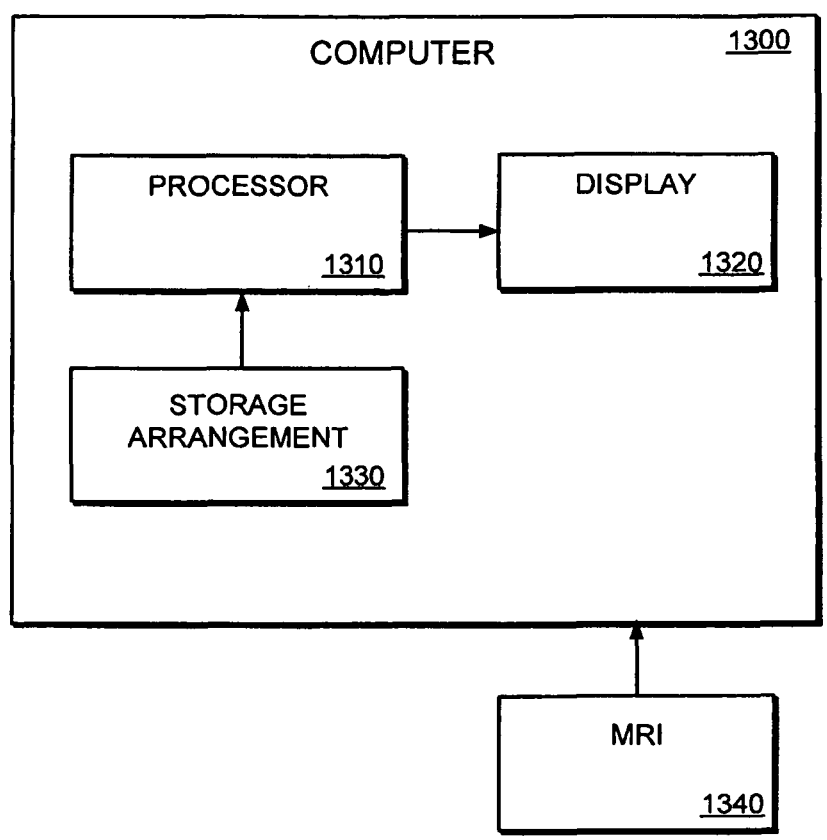
FIG. 13 is an illustration of an exemplary block diagram of an exemplary system in accordance with certain exemplary embodiments of the present disclosure.

FIG. 13 illustrates a block diagram of an exemplary embodiment of a system according to the present disclosure. A computer 1300 can be provided having a processor 1310 which can be configured or programmed to perform the exemplary steps and/or procedures of the exemplary embodiments of the techniques described above. For example, an external device, such as a system which can include an MRI component 1340, can provide measurements to the processor 1310. Such data can be associated with, for example, at least one portion of an anatomical structure. Other sensors and/or external devices or arrangements can be used to provide various type of data, e.g., external processors, biological sensors, etc. According to one exemplary embodiment of the present disclosure, the data can be stored in a storage arrangement 1330 (e.g., hard drive, memory device, such as RAM, ROM, memory stick, floppy drive, other tangible computer-accessible medium, etc.). The processor 1310 can access the storage arrangement 1330 to execute a computer program or a set of instructions (stored on or in the storage arrangement 1330) which perform the procedures according to the exemplary embodiments of the present disclosure.

Thus, e.g., when the processor 1310 performs such instructions and/or computer program, the processor can be configured to effectuate exemplary procedures according to the present disclosure, as described above herein. For example, the processor 1310 can receive information from the MRI 1340 relating to the diffusivity of a sample. This information can be received directly from the MRI 1340 or accessed from the storage arrangement. The processor 1310 can then determine information relating to a permeability of a membrane and/or a measure of a total surface area of a membrane (or membranes) in a sample as a function of the received information.

A display 1320 can also be provided for or in the exemplary system of FIG. 13. The storage arrangement 1330 and the display 1320 can be provided within the computer 1300 or external from the computer 1300. The information received by the processor 1310 and the information determined by the processor 1310, as well as the information stored on the storage arrangement 1330 can be displayed on the display 1320 in a user-readable format.

Figure 14:
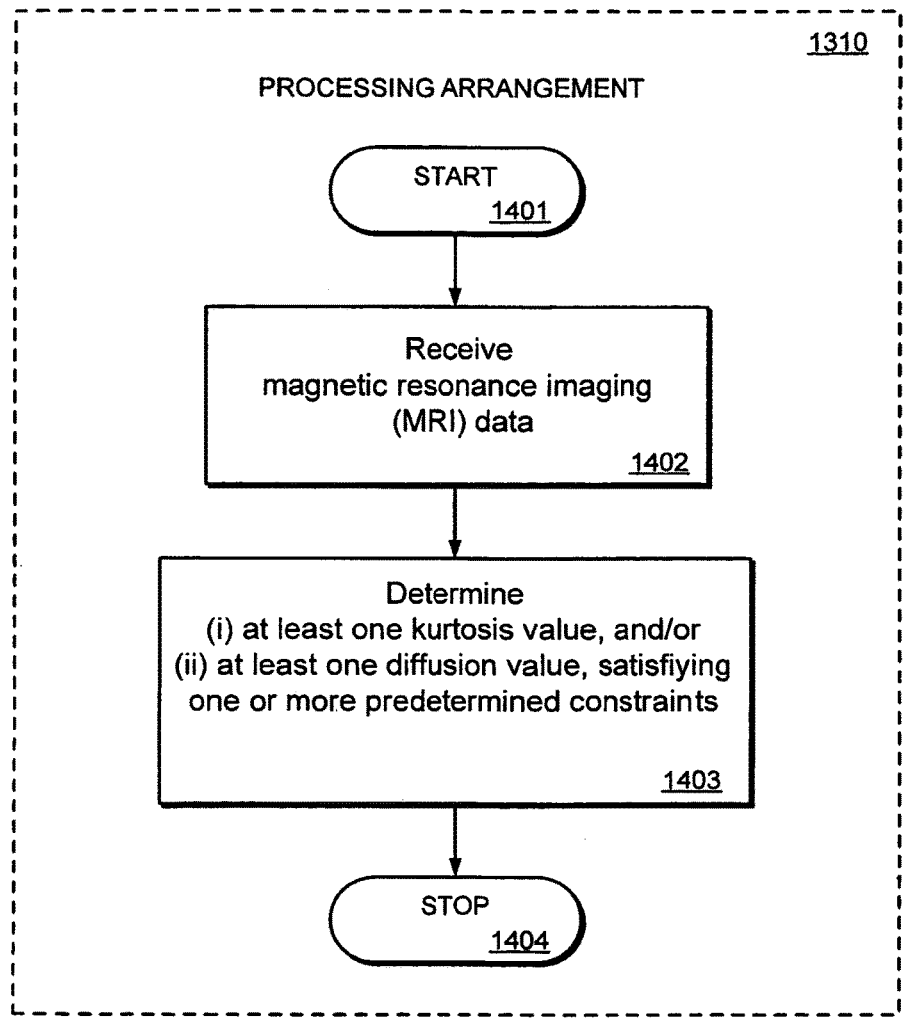
FIG. 14 is an illustration of an exemplary flow diagram of method in accordance with certain exemplary embodiments of the present disclosure.

In addition, an exemplary method/procedure in accordance with certain exemplary embodiments of the present disclosure can be provided that can be used to facilitate an estimation of tensors and/or tensor-derived measures in diffusional kurtosis imaging (DKI). For example, as illustrated in FIG. 14, an exemplary hardware processing arrangement which can utilize an exemplary procedure according to the present disclosure can, starting at subprocess 1401, can be used to receive MRI data in subprocess 1402. Then, in subprocess 1403, the exemplary hardware processing arrangement can determine (i) at least one kurtosis value and/or (ii) at least one diffusion value, satisfying one or more predetermined constraints, for example.

Further Exemplary Embodiments for Estimation of Tensors and Tensor-Derived Measures in DKI Diffusional kurtosis imaging (DKI) can enable characterization of non-Gaussian diffusion of water molecules in biological tissues. The diffusion and kurtosis tensors parameterizing the DKI model can be typically estimated via unconstrained least squares (LS) methods. In the presence of noise, motion, and imaging artifacts, these methods can be prone to producing physically and/or biologically implausible tensor estimates.

The exemplary embodiment of the present disclosure can address this deficiency by formulating the estimation problem as linearly constrained linear LS, where the constraints ensure acceptable tensor estimates. An exemplary solution to this problem can be found via convex quadratic programming methods or through a fast heuristic algorithm. Mean kurtosis maps obtained from in vivo brain images demonstrate the utility of the exemplary tensor estimation algorithms. The heuristic algorithm can be beneficial in real-time situations where run time can be crucial. The computationally more demanding quadratic programming-based method can be more flexible, allowing for an arbitrary number of diffusion weightings and different gradient sets for each diffusion weighting.

Further, substantially exact closed-form expressions for radial and mean kurtoses can be presented, which can replace previous approximate expressions. The new tensor estimation methods along with the tensor-derived metrics provide a robust framework for the clinical application of DKI.

Exemplary Constrained LS Formulation

For direction vector n and diffusion weighting b, the diffusion signal intensity S(n,b) can be written as $$\ln\left[\frac{S(n,b)}{S_0}\right] = -b\sum_{i=1}^{3}\sum_{j=1}^{3}n_i n_j D_{ij} + \frac{1}{6}b^2\overline{D}^2\sum_{i=1}^{3}\sum_{j=1}^{3}\sum_{k=1}^{3}\sum_{l=1}^{3}n_i n_j n_k n_l W_{ijkl} \quad [47]$$

where $S_0$ is the signal intensity for b=0, $D_{ij}$ and $W_{ijkl}$ can be the elements of the second-order diffusion tensor D and fourth-order kurtosis tensor W, respectively, and $\overline{D}=(\frac{1}{3})$ tr(D) is mean diffusivity, where tr(.) denotes matrix trace. For the classic Stejskal-Tanner sequence, the b-value is given by b=$(\gamma\delta g)^2(\Delta-\delta/3)$, where $\Delta$ is the diffusion time, $\delta$ is the pulse duration, g is the diffusion-sensitizing gradient amplitude, and $\gamma$ is the nuclear spin gyromagnetic ratio. Diffusivity D(n) and kurtosis K(n) along direction n can be given by $$D(n) = \sum_{i=1}^{3}\sum_{j=1}^{3}n_i n_j D_{ij}, \quad [48]$$

and $$K(n) = \frac{\overline{D}^2}{D(n)^2}\sum_{i=1}^{3}\sum_{j=1}^{3}\sum_{k=1}^{3}\sum_{l=1}^{3}n_i n_j n_k n_l W_{ijkl}. \quad [49]$$

Both D and W can be symmetric, that is, they can be invariant to permutations of their indices. Consequently, D has 6 and W has 15 independent parameters.

To ensure that the diffusivity and kurtosis parameters can be physically and biologically plausible, D(n) and K(n) can satisfy $$D(n) \geq 0 \quad [50]$$
$$\forall n,$$

and

-continued $$K_{max}(n) \geq K(n) \geq K_{min} \quad \forall n, \text{ and} \quad [51]$$

$$K_{max}(n) = \frac{C}{b_{max}D(n)}, \quad 3 \geq C \geq 0. \quad [52]$$

The constraint in exemplary Equation [50] ensures that D satisfies the necessary condition for non-negative definiteness. Parameter $K_{min}$ is a constant in the [−2, 0] range, with −2 being the theoretically feasible minimum kurtosis, and 0 being the typical choice guaranteeing a super-Gaussian displacement distribution commonly observed in the brain. The constraint on the maximum K(n) ensures that S(n,b) is a monotonically decreasing function of b in the range of b-values used for image acquisition.

For example, one of the objectives in the estimation problem is to determine D and W such that the right-hand side of exemplary Equation [47] closely matches its left-hand side, while the constraints in exemplary Equations [50] and [51] can be satisfied. The estimation problem can therefore be formulated as Minimize $\|AX-B\|^2$ such that $CX \leq d$, [53]

where $$X = [D_{22} D_{33} D_{12} D_{13} D_{23} V_{1111} \ldots V_{1112} \ldots V_{1122} \ldots V_{1233}]^T \quad [54]$$

is a 21×1 vector of unknowns, and $$V_{ijkl} = \overline{D}^2 W_{ijkl}. \quad [55]$$

The change of variables in exemplary Equation [55] is made to permit a linear LS formulation.

Matrix A can be given by $$A = \begin{bmatrix} -b_1 A_D^{(1)} & \frac{1}{6} b_1^2 A_K^{(1)} \\ \vdots & \vdots \\ -b_M A_D^{(M)} & \frac{1}{6} b_M^2 A_K^{(M)} \end{bmatrix}, \quad [56]$$

where M is the number of nonzero b-values, and row k of $A_D^{(m)}$ and $A_K^{(m)}$ can be given by $$[A_D^{(m)}]_k = [(n_{k1}^{(m)})^2 (n_{k2}^{(m)})^2 (n_{k3}^{(m)})^2 n_{k1}^{(m)} n_{k2}^{(m)} n_{k1}^{(m)} n_{k3}^{(m)} n_{k2}^{(m)} n_{k3}^{(m)}], \quad [57]$$

$$[A_K^{(m)}]_k = [(n_{k1}^{(m)})^4 \ldots 4(n_{k1}^{(m)})^3 n_{k2} \ldots 6(n_{k1}^{(m)})^2 (n_{k2}^{(m)})^2 \ldots 12 n_{k1}^{(m)} n_{k2}^{(m)} (n_{k3}^{(m)})^2],$$

Where $$n_k^{(m)} = [n_{k1}^{(m)} n_{k2}^{(m)} n_{k3}^{(m)}]^T.$$

Note that each diffusion weighting $b_M$ can correspond to a Distinct gradient set $N^{(m)} = \{n_1^{(m)}, \ldots, n_{N_m}^{(m)}\}$. The number of rows of A is thus given by $$N = \sum_{m=1}^{M} N_m. \quad [58]$$

Vector B can be given by $$B = [\ln(S_1/S_0) \ldots \ln(S_N/S_0)]^T, \quad [59]$$

where $S_k = S(n_i^{(m)}, b_m)$, is the diffusion signal intensity for gradient direction $n_i^{(m)}$ and diffusion weighting $b_m$, and $$k = \sum_{j=1}^{m-1} N_j + i. \quad [60]$$

Matrix C representing the linear constraints can be given by $$c = \begin{bmatrix} -A_D & 0 \\ 0 & -A_K \\ -(C/b_{max})A_D & A_K \end{bmatrix}, \quad [61]$$

where $$A_D = \begin{bmatrix} A_D^{(1)} \\ \vdots \\ A_D^{(M)} \end{bmatrix} \quad [62]$$

and $$A_K = \begin{bmatrix} A_K^{(1)} \\ \vdots \\ A_K^{(M)} \end{bmatrix}. \quad [63]$$

Vector d can be given by $$d = \begin{bmatrix} 0 & K_{min}D(n_1^{(1)})^2 & \ldots & K_{min}D(n_{N_1}^{(1)})^2 & \ldots & K_{min}D(n_1^{(M)})^2 & \ldots & K_{min}D(n_{N_M}^{(M)})^2 & 0 \end{bmatrix}^T, \quad [64]$$

where the zero vectors can be 1×N-dimensional.

For a typical choice $K_{min}=0$, exemplary Equation [53] can provide a substantially exact formulation of the estimation problem. If $K_{min} \neq 0$, the $D(n_n^{(m)})$ terms in d can need to be approximated. This can be accomplished, for example, via estimating D once and plugging that estimate into exemplary Equation [48]. The estimate of D can be obtained from the ULLS estimate of X, denoted as $\hat{X}$, given by $$\hat{X}=A^+B, \qquad [65]$$

where $A^+$ denotes the pseudoinverse of A.

The condition number of A, which can be defined as the ratio of its largest singular value to its smallest singular value, can become large for some choices of gradient sets and b-values, which in turn increases the sensitivity of the solution to measurement errors. To mitigate this exemplary problem, columns of A can be scaled to have an $L_2$ norm of 1. Once X is found using the scaled A, the actual solution can be determined by dividing each element $X_i$ by the $L_2$ norm of the i-th column of the original A.

Exemplary Quadratic Programming (CLLS-QP) Algorithm

An exemplary problem which can be defined by exemplary Equation [53] is a convex quadratic programming problem whose solution can be determined via standard algorithms. Two common classes of algorithms for solving this problem can be active set and interior-point methods. The active set method was used, which can work as follows. First, the algorithm is initialized with a feasible point, if one exists. A feasible point, defined as a point that satisfies the constraints in exemplary Equation [53], can be found via linear programming. According to certain exemplary embodiments, the ULLS solution of exemplary Equation [65] can be used first as a potential feasible point. If this point is feasible, it is also the solution to the CLLS problem. If the point is not feasible, then the algorithm uses the feasible point found via linear programming.

In the second phase, an iterative sequence of feasible points can be generated such that they converge to the optimal solution. At each iteration, an estimate of the active constraints in exemplary Equation [53] is maintained. Active constraints can be a subset of the constraints that can be actually enforced, that is, they can be the ones that become equality constraints. As the algorithm/procedure proceeds, the set of active constraints is updated by sequentially adding the active and removing the inactive constraints from the set.

Exemplary Heuristic (CLLS-H) Algorithm/Procedure

Alternatively, the exemplary heuristic procedure described below can be used to estimate D and W such that the constraints of exemplary Equations [50] and [51] can be approximately satisfied. This algorithm assumes that exactly two nonzero b-values can be used, and that the gradient directions can be the same for both b-values; that is, $N^{(1)}=N^{(2)}=\{n_1, \ldots, n_N\}$. In the first step, $D(n_i)$ and $K(n_i)$ can be first determined from $S(n_i,b_1)$ and $S(n_i,b_2)$. Then, the constraints of exemplary Equations [50] and [51] can be imposed on $D(n_i)$. Next, the constrained $D(n_i)$ can be used to estimate D, which in turn can be used to re-estimate $D(n_i)$. Finally, $K(n_i)$ and the re-estimated $D(n_i)$ can be used to compute W.

Along direction $n_i$, $D_i=D(n_i)$ and $K_i=K(n_i)$ can be given by $$D_i = \frac{b_2 D_i^{(1)} - b_1 D_i^{(2)}}{b_2 - b_1}, \qquad [66]$$

and $$K_i = 6\frac{D_i^{(1)} - D_i^{(2)}}{(b_2 - b_1)D(n_i)^2}, \qquad [67]$$

where $$D_i^{(1)} = \frac{-\ln(S(n_i, b_1)/S_0)}{b_1}, \qquad [68]$$

$$D_i^{(2)} = \frac{-\ln(S(n_i, b_2)/S_0)}{b_2}.$$

Next, a set of rules is applied to constrain $D_i$:
If $D_i \leq 0$, set $D_i=0$.
Otherwise, if $D_i^{(1)}<0$, set $D_i=0$.
Otherwise, if $D_i>0$ and $K_i<K_{min}$,
If $K_{min}=0$, set $D_i=D_i^{(1)}$.
Otherwise, set $$D_i = \frac{1}{x}\left[\sqrt{1 + 2xD_i^{(1)}} - 1\right] \qquad [69]$$

where $$x = -\frac{1}{3}K_{min}b_1.$$

Otherwise, if $D_i>0$ and $K_i>K_{max_i}$, where $K_{max}=K(n_i)$, set $$D_i = \frac{D_i^{(1)}}{1 - Cb_1/6b_{max}} \qquad [70]$$

where $b_{max}=\max(b_1,b_2)$.

From the constrained $D_i$ set, D can be estimated as $$\hat{X}_D = A_D^+ b_D, \qquad [71]$$

where $\hat{X}_D$ is the ULLS estimate of $X_D=[D_{11}\ D_{22}\ D_{33}\ D_{12}\ D_{13}\ D_{23}]^T$, and $b_D=[D_1 \ldots D_N]^T$.

The re-estimated $b_D^{(R)}$ is then obtained as $b_D^{(R)}=A_D\hat{X}_D$. The re-estimation step has a noise removal effect on $b_D$ by forcing it to be consistent with $\hat{X}_D$. Next, $D_i^{(R)}$ can be used to obtain $K_i^{(R)}$ using the following rules:

If $D_i^{(R)}>0$, set $$K_i^{(R)} = 6\frac{D_i^{(R)} - D_i^{(2)}}{b_2(D_i^{(R)})^2}, \qquad [72]$$

where $K_i^{(R)}$ denotes kurtosis $n_i$ along estimated using $D_i^{(R)}$.
Otherwise, set $H_i^{(R)}=0$.
If $K_i>K_{max_i}^{(R)}$, set $K_i=K_{max_i}^{(R)}$.
If $K_i<K_{min}$, set $K_i=K_{min}$.
Further, the kurtosis tensor can be estimated as $$X_K = \frac{1}{\overline{D}^2} A_K^+ b_K \qquad [73]$$

where $\hat{X}_K$ is the ULLS estimate of $X_K=[W_{1111} \ldots W_{1112} \ldots W_{1122} \ldots W_{1233}]^T$, and $b_K=[(D_1^{(R)})^2 K_1 \ldots (D_N^{(R)})^2 K_N]^T$.

Exemplary Tensor-Derived Scalar Measures

Let $\lambda_1>\lambda_2>\lambda_3$ denote the eigenvalues of D. The most common scalar measures obtained from the diffusion tensor can be given by $$\overline{D} = \frac{1}{3}(\lambda_1 + \lambda_2 + \lambda_3) \quad [74]$$

and $$D_\parallel = \lambda_1, \quad [75]$$

and $$D_\perp = \frac{1}{2}(\lambda_2 + \lambda_3) \quad [76]$$

where $D_\parallel$ and $D_\perp$ denote the axial and radial diffusivities, respectively. The fractional anisotropy (FA) is given by $$FA = \sqrt{\frac{(\lambda_1 - \lambda_2)^2 + (\lambda_1 - \lambda_3)^2 + (\lambda_2 - \lambda_3)^2}{\sqrt{2(\lambda_1^2 + \lambda_2^2 + \lambda_3^2)}}}. \quad [77]$$

The MK is the diffusional kurtosis averaged over all directions. In a reference frame that diagonalizes D, it can be calculated as (see the Appendix for the derivation)

$$\overline{K} = A_{1111}(\lambda_1, \lambda_2, \lambda_3)\tilde{W}_{1111} + A_{1111}(\lambda_2, \lambda_1, \lambda_3)\tilde{W}_{2222} + \quad [78]$$
$$A_{1111}(\lambda_3, \lambda_2, \lambda_1)\tilde{W}_{3333} + 6A_{2233}(\lambda_1, \lambda_2, \lambda_3)\tilde{W}_{2233} +$$
$$6A_{2233}(\lambda_2, \lambda_1, \lambda_3)\tilde{W}_{1133} + 6A_{2233}(\lambda_3, \lambda_2, \lambda_1)\tilde{W}_{1122}$$

where $\tilde{W}_{ijkl}$ can be the elements of the kurtosis tensor in the rotated frame and can be given by $$\tilde{W}_{ijkl} = \sum_{i,j,k,l=1}^{3} R_{ii'} R_{jj'} R_{kk'} R_{ll'} W_{i'j'k'l'}, \quad [79]$$

with $R_{ij}$ being the j-th component of the eigenvector of D corresponding to $\lambda_i$. Coefficients $A_{1111}$ and $A_{2233}$ can be given by $$A_{1111}(\lambda_1, \lambda_2, \lambda_3) = \frac{(\lambda_1 + \lambda_2 + \lambda_3)^2}{18(\lambda_1 - \lambda_2)(\lambda_1 - \lambda_3)} \left[\frac{\sqrt{\lambda_2\lambda_3}}{\lambda_1} R_F\left(\frac{\lambda_1}{\lambda_2}, \frac{\lambda_1}{\lambda_3}, 1\right) + \frac{3\lambda_1^2 - \lambda_1\lambda_2 - \lambda_1\lambda_3 - \lambda_2\lambda_3}{3\lambda_1\sqrt{\lambda_2\lambda_3}} R_D\left(\frac{\lambda_1}{\lambda_2}, \frac{\lambda_1}{\lambda_3}, 1\right) - 1\right] \quad [80]$$

and $$A_{2233}(\lambda_1, \lambda_2, \lambda_3) = \frac{(\lambda_1 + \lambda_2 + \lambda_3)^2}{18(\lambda_2 - \lambda_3)^2} \left[\frac{\lambda_2 + \lambda_3}{\sqrt{\lambda_2\lambda_3}} R_F\left(\frac{\lambda_1}{\lambda_2}, \frac{\lambda_1}{\lambda_3}, 1\right) + \frac{2\lambda_1 - \lambda_2 - \lambda_3}{3\sqrt{\lambda_2\lambda_3}} R_D\left(\frac{\lambda_1}{\lambda_2}, \frac{\lambda_1}{\lambda_3}, 1\right) - 2\right], \quad [81]$$

where $R_F$ and $R_D$ can be Carlson's elliptic integrals defined as $$R_F(x,y,z) = \frac{1}{2}\int_0^\infty (t+x)^{-1/2}(t+y)^{-1/2}(t+z)^{-1/2} dt \quad [82]$$

and $$R_D(x,y,z) = \frac{3}{2}\int_0^\infty (t+x)^{-1/2}(t+y)^{-1/2}(t+z)^{-3/2} dt \quad [83]$$

As there can be highly efficient numerical algorithms for calculating Carlson's elliptic integrals, exemplary Equations [80] and [81] can be used for fast computation of the MK. Note that when two or more of the eigenvalues of D coincide, $A_{1111}$ and $A_{2233}$ have removable singularities whose treatment is discussed in the Appendix.

The axial kurtosis (AK) $K_\parallel$ is the diffusional kurtosis in the direction of the highest diffusion. In a reference frame that diagonalizes D, it is simply given by $$K_\parallel = \frac{(\lambda_1 + \lambda_2 + \lambda_3)^2}{9\lambda_1^2} \tilde{W}_{1111}. \quad [84]$$

The radial kurtosis (RK) $K_\perp$ is the mean diffusional kurtosis perpendicular to the direction of the highest diffusion. In a reference frame that diagonalizes D, it is given by (see the Appendix for the derivation)

$$K_\perp = C_{2222}(\lambda_1,\lambda_2,\lambda_3)\tilde{W}_{2222} + C_{2222}(\lambda_1,\lambda_3,\lambda_2)\tilde{W}_{3333} + 6C_{2233}(\lambda_1,\lambda_2,\lambda_3)\tilde{W}_{2233}. \quad [85]$$

where $$C_{2222}(\lambda_1, \lambda_2, \lambda_3) = \frac{(\lambda_1 + \lambda_2 + \lambda_3)^2}{18\lambda_2(\lambda_2 - \lambda_3)^2}\left(2\lambda_2 + \frac{\lambda_3^2 - 3\lambda_2\lambda_3}{\sqrt{\lambda_2\lambda_3}}\right) \quad [86]$$

and $$C_{2233}(\lambda_1, \lambda_2, \lambda_3) = \frac{(\lambda_1 + \lambda_2 + \lambda_3)^2}{18(\lambda_2 - \lambda_3)^2}\left(\frac{\lambda_2 + \lambda_3}{\sqrt{\lambda_2\lambda_3}} - 2\right). \quad [87]$$

Exemplary Magnetic Resonance Imaging Procedure

An exemplary DKI scan was performed on a healthy volunteer using a 3 T Siemens Trio system with an 8-channel head coil. Diffusion-weighted images were acquired along 30 gradient directions with a twice-refocused spin-echo planar imaging sequence (TR=2300, TE=109 ms, matrix=128×128, FOV=256×256 mm$^2$, 15 slices, slice thickness=2 mm, gap=2 mm, NEX=6 for b=0, NEX=2 for b=500, 1000, 1500, 2000, 2500 s/mm$^2$) The total acquisition time was about 12 minutes.

Exemplary Processing Pipeline

The pipeline for estimating the tensor-derived measures is shown in FIG. 15. In the first stage of processing 1501, the gradient images 1500 can be optionally smoothed using a linear filter with the Gaussian kernel to reduce the impact of noise and misregistration. Next, noise subtraction can be performed in subprocess 1502 using an optionally smoothed noise image 1505. Noise subtraction can aim to correct for the bias introduced by taking the magnitude of the Gaussian noise. The estimate of the signal D at each voxel is obtained as W, where S and n denote smoothed image intensity and noise image intensity at that voxel. Next, in subprocess 1503, D and W can be estimated using the CLLS-QP algorithm, and the scalar measures 1506 can be obtained from the tensors. The pipeline was implemented in-house in the MATLAB environment (http://www.mathworks.com). The program, designated as Diffusional Kurtosis Estimator (DKE), is available upon request from the corresponding author.

The parameters used with exemplary DKE can be as follows: the Gaussian kernel used for smoothing the gradient images had a full width at half maximum of 2.5 mm in the imaging plane; no noise image was used; $K_{min}=0$; and $C=3$. The tensors were also estimated using the CLLS-H and ULLS algorithms following smoothing of gradient images. Three processing scenarios were considered: in the first case, the MK map was obtained using all the available gradient images; in the second case, it was estimated using all of the gradient images for b=1000, 2000 s/mm²; and in the third scenario, it was obtained based on 6 of b=1000 s/mm² and all of b=2000 s/mm² gradient images. The MK map obtained using ULLS under the first scenario was used as "ground truth" to evaluate the maps estimated under the other scenarios. The second scenario can correspond to exemplary current clinical protocol, and the third scenario was conjured up as a potential candidate for future clinical acquisitions.

Further Exemplary Results

Exemplary Table 1 shows the total processing time for generating the scalar tensor-derived measures using all the gradient images for b=1000, 2000 s/mm² The table also summarizes the features of the tensor estimation algorithms.

Figures 16A, 16B, 16C:
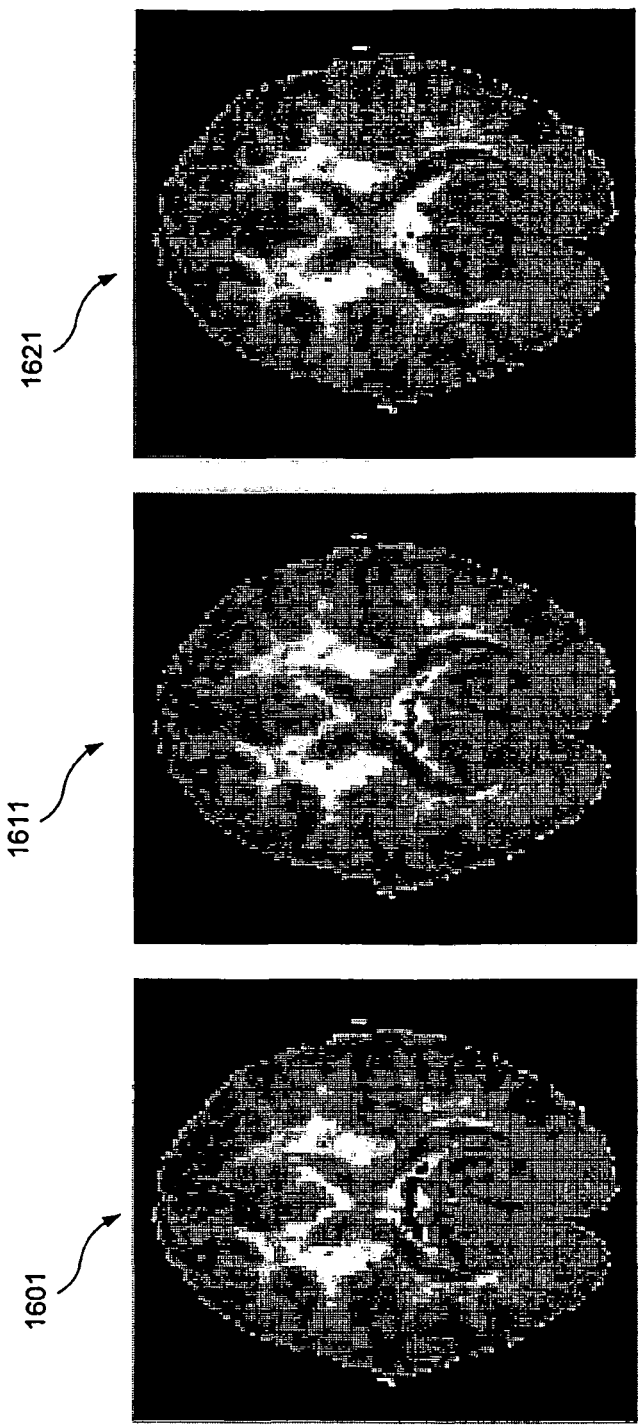
FIG. 16(a) is an exemplary MK image obtained using 30 gradient directions for b=1000, 2000 s/mm$^2$ and ULLS, in accordance with certain exemplary embodiments of the present disclosure.
FIG. 16(b) is an exemplary MK image obtained using 30 gradient directions for b=1000, 2000 s/mm$^2$ and CLLS-H, in accordance with certain exemplary embodiments of the present disclosure.
FIG. 16(c) is another exemplary MK image also obtained using 30 gradient directions for b=1000, 2000 s/mm$^2$ and CLLS-QP, in accordance with other exemplary embodiments of the present disclosure.
Figures 17A, 17B, 17C:
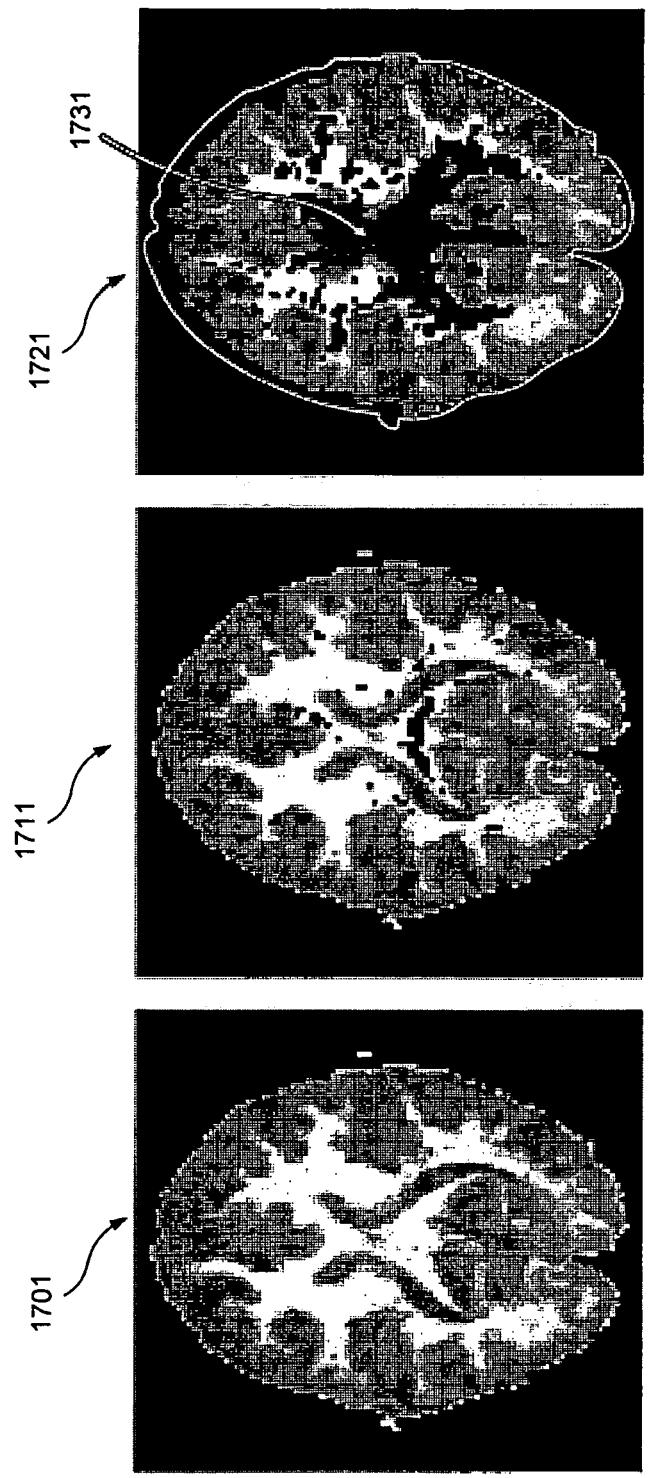
FIG. 17(a) is an exemplary image showing voxels where the diffusion and kurtosis tensors estimated using ULLS violate the constraints on directional diffusivities, in accordance with certain exemplary embodiments of the present disclosure.
FIG. 17(b) is another exemplary image of voxels where the diffusion and kurtosis tensors estimated using ULLS also violate the constraints on minimum directional kurtoses, in accordance with other exemplary embodiments of the present disclosure.
FIG. 17(c) is another exemplary image of voxels where the diffusion and kurtosis tensors estimated using ULLS also violate the constraints on maximum directional kurtoses, in accordance with further exemplary embodiments of the present disclosure.

FIGS. 16(a)-16(c) show the exemplary MK maps 1601, 1611, 1621 obtained using all the gradient images for b=1000, 2000 s/mm² The region with the most noticeable change in the estimated MK is the corpus callosum, where the voxels with the incorrectly estimated MK values appear darker than their neighbors. The CLLS-H algorithm corrects the MK values for some of these voxels, whereas the CLLS-QP corrects all of the voxels. FIGS. 17(a)-17(c) show exemplary maps 1701, 1711, 1721, respectively. As illustrated in FIGS. 17(a)-17(c), voxels 1731 where tensor estimates obtained via ULLS can violate the constraints in exemplary Equations [50] and [51]. As indicated, the constraints on directional diffusivities cannot be violated in this case, in accordance with certain exemplary embodiments of the present disclosure.

FIGS. 18(a) and 18(b) show the MK maps 1801, 1811 estimated using 6 of b=1000 s/mm² and all of b=2000 s/mm² gradient images, and FIGS. 19(a)-19(c) show the voxels 1931 show exemplary maps 1901, 1911, 1921, respectively, for which the constraints can be violated. The highlighted voxels 1931 can be those for which at least one constraint has been violated, in accordance with certain exemplary embodiments of the present disclosure. In this exemplary case, the voxels 1931 with the incorrect MK values can be scattered in many parts of white matter in addition to the corpus callosum. Further, due to the different numbers of gradient directions, use of the exemplary CLLS-H algorithm is likely not applicable.

FIGS. 20(a)-20(c) show exemplary maps 2001, 2011, 2021 estimated using exemplary expressions for the MK and RK along with the map for AK. Intensity scales 2002, 2012, 2022 are provided in FIGS. 20(a)-20(c), respectively. As illustrated, the exemplary images 2001, 2011, 2021 can be displayed with different scales in accordance with certain exemplary embodiments of the present disclosure.

Exemplary Tables 2(a) and 2(b) show the root mean-square error (RMSE) between the estimated MK maps using ULLS and all gradient images, and the maps estimated with ULLS, CLLS-H, and CLLS-QP algorithms using a portion of the gradient images.

EXEMPLARY TABLE 1

Exemplary feature comparison between the ULLS, heuristic CLLS, and CLLS. Run time was obtained for the case where all gradient images for b = 1000, 2000 s/mm² were used and includes the input/output time. The Run time was obtained using a Dell Optiplex desktop equipped with a 3.0 GHz Pentium Core 2 Duo processor.

|  | ULLS | Heuristic CLLS | CLLS |
|---|---|---|---|
| Run time | 130 s | 136 s | 335 s |
| Number of b values | Any | 2 nonzero | Any |
| Number of gradient directions per b value | Any | Equal | Any |

EXEMPLARY TABLE 2(a)

Exemplary root mean-square error (RMSE) between the ULLS-estimated MK map with the available gradient images and the MK map estimated using 30 gradient images for b = 1000, 2000 s/mm².

| Algorithm | ULLS | CLLS-H | CLLS-QP |
|---|---|---|---|
| RMSE | 0.0344 | 0.0295 | 0.0301 |

EXEMPLARY TABLE 2(b)

Exemplary root mean-square error (RMSE) between the ULLS-estimated MK map with the available gradient images and the MK map estimated using 6 gradient images for b = 1000 s/mm² and 30 gradient images for b = 2000 s/mm².

| Algorithm | ULLS | CLLS-QP |
|---|---|---|
| RMSE | 0.2162 | 0.0519 |

The exemplary voxels 1631 illustrated in FIGS. 16(a)-16(c) and FIGS. 18(a) and 18(b) where CLLS-H and CLLS-QP produce visually improved MK estimates can be those for which ULLS yields a NPD or a nearly NPD estimate of D and/or the constraints on the minimum and maximum kurtoses can be violated. In these voxels, which can most likely to occur in high FA regions such as the corpus callosum, $\lambda_3$ has a small magnitude, which in turn increases the sensitivity of the ULLS estimate of D to noise. It is well-known that imaging noise causes $\lambda_3$ to be underestimated. The constraints in exemplary Equations [50] and [51] force a larger $\lambda_3$, yielding a more reasonable estimate of D. Assessing the impact of the constraints on W is more challenging; however, it should be emphasized that the constraints in exemplary Equation [51] can be necessary for obtaining correct MK estimates. This is confirmed by examining the voxels in the corpus callosum in FIG. 16, where the estimated D satisfies the constraints on directional diffusivities, whereas the estimated W violates the constraints on directional kurtoses, eventually yielding incorrect MK estimates.

Exemplary Tables 2(a) and 2(b) provide further confirmation of the improvement that the CLLS algorithms offer. The CLLS-H and CLLS-QP algorithms achieve comparable RMSE, and both outperform the ULLS. The RMSE improvement is particularly striking in the scenario with 6 b=1000 s/mm² gradient images. It should be noted that as the "ground truth" used in the calculations was based on the ULLS algorithm, which does not satisfy the constraints in exemplary Equations [50] and [51], the RMSE estimates can be biased in favor of the ULLS and CLLS-H algorithms.

The CLLS-H algorithm/procedure/method can strike a balance between complexity and accuracy by correcting the MK in most of the voxels that violate the constraints, while doing so at a negligible 5% overhead compared to the ULLS, as illustrated in, e.g., exemplary Table 1. Thus, the CLLS-H method/procedure can be beneficial in real-time situations where run time is crucial. On the other hand, the CLLS-QP approach removes all such voxels, but it has a much longer run time. It should be noted that while the improvement offered by CLLS-QP comes at the expense of increased algorithm complexity and consequently higher run time, it is straightforward to speed up the computations via parallelization.

A limitation of the formulation in exemplary Equation [53] is that it ensures that constraints in exemplary Equations [50] and [51] can be satisfied along all imaged gradient directions, rather than all possible directions Imposing the latter constraints is more challenging and requires a deeper understanding of the kurtosis tensor. A practically viable alternative is to estimate the tensors using either of the CLLS algorithms and then check if the solution satisfies the constraints along other directions. The directions of the eigenvectors of D can be of the most interest as exemplary Equations [78] and [85] can be explicit functions of the kurtosis tensor elements along these directions. If the solution does not satisfy the constraints along these directions, then these constraints can be added to the set of constraints in exemplary Equations [50] and [51] and the problem re-solved. This exemplary procedure can be repeated until the solution satisfies the constraints.

Further, as the expressions for RK and MK used for estimating the maps in Figure A6 represent the exact values of these parameters, they more accurately quantify the diffusional kurtosis characteristics of the tissue. Additionally, the exemplary radial kurtosis is more robust to noise than may otherwise be achieved as it represents the mean kurtosis along all directions perpendicular to the direction of maximum diffusivity, whereas the previous expression in depends on two perpendicular directions.

The exemplary embodiments of the present disclosure can describes a CLLS formulation for the estimation of diffusion and kurtosis tensors parameterizing the DKI model. The exemplary CLLS formulation can offer a computationally tractable means for tensor estimation via minimizing a convex cost function that ensures that the estimated diffusivities and kurtoses along the imaged gradient directions remain within a physically and biologically plausible range. Two procedures can be provided for minimizing the CLLS cost function: a convex quadratic programming (CLLS-QP) method or a heuristic (CLLS-H) algorithm. The CLLS-H algorithm imposes a negligible computational overhead compared to the ULLS algorithm, making it suitable for real-time applications with two b-values and equal numbers of gradients per b-value, whereas the computationally more demanding CLLS-QP algorithm permits an arbitrary number of b-values and different gradient sets per each b-value. The examples using in vivo image data demonstrate the utility of the exemplary CLLS formulation.

One of the advantages of the CLLS approach over ULLS is particularly evident when fewer gradient images can be available. In addition, exact closed-form expressions can be provided which can more accurately represent RK and MK. The exemplary tensor estimation methods along with the new kurtosis measures improve the robustness of the tensor-derived measures, thus facilitating the clinical application of DKI.

An exemplary MK can be calculated from the following:

$$\overline{K} = \sum_{i,j,k,l=1}^{3} A_{ijkl} W_{ijkl}, \qquad [88]$$

where $$A_{ijkl} \equiv \frac{\overline{D}^2}{4\pi} \int_0^\pi d\theta \int_0^{2\pi} d\phi \frac{n_i n_j n_k n_l}{\left(\sum_{p,q=1}^{3} n_p n_q D_{pq}\right)^2} \sin\theta \qquad [89]$$

and $n_i$ is the i-th element of unit direction vector n. MK can be obtained by numerically evaluating the integral in exemplary Equation [89]. However, this can be computationally inefficient if a high degree of accuracy is desired. Described below is an analytic formula for $A_{ijkl}$ that can enable fast computation of the MK.

In a reference frame that diagonalizes D (see, e.g., exemplary Equation [79]), it is possible to write $$\overline{K} = \sum_{i,j,k,l=1}^{3} A_{ijkl} \tilde{W}_{ijkl}, \qquad [90]$$

where $A_{ijkl}$ can be given by $$A_{ijkl}(\lambda_1, \lambda_2, \lambda_3) = \qquad [91]$$
$$\frac{\overline{D}^2}{4\pi} \int_0^\pi d\theta \int_0^{2\pi} d\phi \frac{n_i(\theta,\phi)n_j(\theta,\phi)n_k(\theta,\phi)n_l(\theta,\phi)\sin\theta}{(\lambda_1 \sin^2\theta\cos^2\phi + \lambda_2\sin^2\theta\sin^2\phi + \lambda_3\cos^2\theta)^2},$$

and $n_1(\theta,\phi) = \sin\theta\cos\phi,$ $n_2(\theta,\phi) = \sin\theta\sin\phi,$ $n_3(\theta,\phi) = \cos\theta.$ It can be seen from exemplary Equation [91] that $A_{ijkl}$ is invariant with respect to permutations of its indices. Thus, it is possible to consider only the 15 components $A_{1111}$, $A_{1112}$, $A_{1113}$, $A_{1122}$, $A_{1123}$, $A_{1133}$, $A_{1222}$, $A_{1223}$, $A_{1233}$, $A_{1333}$, $A_{2222}$, $A_{2223}$, $A_{2233}$, $A_{2333}$, and $A_{3333}$. From symmetry of the integrand in exemplary Equation [91], one can show $$0 = A_{1112} = A_{1113} = A_{1123} = A_{1222} = A_{1223} = A_{1233} = A_{1333} = A_{2223} = A_{2333}. \qquad [93]$$

This can leave only 6 nonzero components to consider. It is possible to further reduce this number by noting the symmetries $$A_{1111} = (\lambda_1, \lambda_2, \lambda_3) = A_{2222}(\lambda_2, \lambda_1, \lambda_3) = A_{3333}(\lambda_3, \lambda_2, \lambda_1) \qquad [94]$$

and $$A_{2233} = (\lambda_1, \lambda_2, \lambda_3) = A_{1133}(\lambda_2, \lambda_1, \lambda_3) = A_{1122}(\lambda_3, \lambda_2, \lambda_4) \qquad [95]$$

Hence it can be beneficial to only find analytic expressions for $A_{1111}$ and $A_{2233}$. From these, and by applying conventional integration techniques and also utilizing exemplary Equation [74], the MK can be calculated as prescribed by exemplary Equation [78].

When $\lambda_1=\lambda_2$ or $\lambda_1=\lambda_3$, exemplary Equation [80] has a removable singularity, which can be resolved with $$\alpha(x) \equiv \begin{cases} \frac{1}{\sqrt{x}}\mathrm{arctanh}(\sqrt{x}), & \text{if } x > 0, \\ \frac{1}{\sqrt{-x}}\mathrm{arctan}(\sqrt{-x}), & \text{if } x < 0. \end{cases} \quad [98]$$

When $\lambda_2=\lambda_3$, exemplary Equation [81] has a removable singularity. This can be resolved with $$A_{1111}=(\lambda_1,\lambda_1,\lambda_3)=3A_{2233}(\lambda_3,\lambda_1,\lambda_1) \text{ or } A_{1111}=(\lambda_1,\lambda_2,\lambda_1)=3A_{2233}(\lambda_2,\lambda_1,\lambda_1). \quad [96]$$

where $$A_{2233} = (\lambda_1, \lambda_3, \lambda_3) = \quad [97]$$

$$\frac{(\lambda_1+2\lambda_3)^2}{144\lambda_3^2(\lambda_1-\lambda_3)^2}\left[\lambda_3(\lambda_1+2\lambda_3)+\lambda_1(\lambda_1-4\lambda_3)\alpha\left(1-\frac{\lambda_1}{\lambda_3}\right)\right],$$

For the exemplary case when $\lambda_1=\lambda_2=\lambda_3$, can simply yield $$A_{1111} = \frac{1}{5} \text{ and } A_{2233} = \frac{1}{15}. \quad [99]$$

The radial kurtosis (RK) $K_\perp$ is the mean diffusional kurtosis perpendicular to the direction of the highest diffusion. In a reference frame that diagonalizes D, it is given by $$K_\perp = \sum_{i,j,k,l=1}^{3} C_{ijkl}\tilde{W}_{ijkl}, \quad [100]$$

where $$C_{ijkl}(\lambda_1, \lambda_2, \lambda_3) = \frac{\bar{D}^2}{2\pi}\int_0^{2\pi} d\phi \frac{n_i(\phi)n_j(\phi)n_k(\phi)n_l(\phi)}{(\lambda_2\cos^2\phi+\lambda_3\sin^2\phi)^2}, \quad [101]$$

and $$\begin{aligned} n_1(\phi) &= 0, \\ n_2(\phi) &= \cos\phi, \\ n_3(\phi) &= \sin\phi. \end{aligned} \quad [102]$$

It can be seen from exemplary Equation [101] that $C_{ijkl}$ is invariant with respect to permutations of its indices. Thus, it is possible to consider only the 15 components $C_{1111}$, $C_{1112}$, $C_{1113}$, $C_{1122}$, $C_{1123}$, $C_{1133}$, $C_{1222}$, $C_{1223}$, $C_{1233}$, $C_{1333}$, $C_{2222}$, $C_{2223}$, $C_{2233}$, $C_{2333}$, and $C_{3333}$. From symmetry of the integrand in exemplary Equation [101] and the fact that $n_1(\phi)=0$, one can show $$0=C_{1111}=C_{1112}=C_{1113}=C_{1122}=C_{1123}=C_{1133}=C_{1222}=C_{1223}= \\ C_{1233}=C_{1333}=C_{2223}=C_{2333} \quad [103]$$

This can leave only 3 nonzero components to consider. It is possible to further reduce this number by noting the symmetry $$C_{2222}(\lambda_1,\lambda_2,\lambda_3)=C_{3333}(\lambda_1,\lambda_3,\lambda_2). \quad [104]$$

Hence it can be beneficial to find analytic expressions for $C_{2222}$ and $C_{2233}$. From these, the RK can be obtained as prescribed by exemplary Equation [85], where the integrals $$C_{2222}(\lambda_1, \lambda_2, \lambda_3) = \frac{\bar{D}^2}{2\pi}\int_0^{2\pi} d\phi \frac{\cos^4\phi}{(\lambda_2\cos^2\phi+\lambda_3\sin^2\phi)^2} \text{ and} \quad [105]$$

$$C_{2233}(\lambda_1, \lambda_2, \lambda_3) = \frac{\bar{D}^2}{2\pi}\int_0^{2\pi} d\phi \frac{\cos^2\phi\sin^2\phi}{(\lambda_2\cos^2\phi+\lambda_3\sin^2\phi)^2} \quad [106]$$

can be elementary forms which lead to exemplary Equations [86] and [87].

For the special case of $\lambda_2=\lambda_3$, exemplary Equations [86] and [87] reduce to:

$$C_{2222}(\lambda_1, \lambda_2, \lambda_2) = \frac{(\lambda_1+2\lambda_2)^2}{24\lambda_2^2} \text{ and} \quad [107]$$

$$C_{2223}(\lambda_1, \lambda_2, \lambda_2) = \frac{(\lambda_1+2\lambda_2)^2}{72\lambda_2^2}. \quad [108]$$

Exemplary White Matter Model for Diffusional Kurtosis Imaging (DKI)

Further, described herein is an exemplary embodiment of an idealized diffusion model of white matter (WM) that can be used for, e.g., DKI analysis, which can allow for quantification of the intra- and extra-axonal diffusivities, the axonal water fraction and the tortuosity of the extra-axonal space. Exemplary embodiments according to the present disclosure can also provide a further physical interpretation of DKI metrics for WM, for example.

Exemplary Discussion

Presuming, for example, that WM is composed of parallel axons that can each be surrounded by a myelin sheath with an along axis diffusion coefficient of $D_a$, it is possible to utilize a perpendicular axon diffusivity of zero since myelinated axons can have a very low permeability and a small radius (~1 µm). Referring to the remainder of the WM as the extra-axonal space (EAS), it is possible to model it as an effective medium with a diffusion coefficient $D_e$ parallel to the axons' axes and a diffusion coefficient $D_e/\lambda$ perpendicular to the axons' axes, where $\lambda$ can represent the tortuosity of the medium. In addition, it is possible to indicate the axonal water fraction (AWF), e.g., the volume fraction of water in the axons relative to the total water volume, by the symbol f. Since it is possible that the protons in myelin do not contribute to the DWI-signal, the system can then comprise two non-exchanging compartments.

For example, the radial and axial diffusion coefficients, $D_\perp$ and $D_\parallel$, and diffusional kurtoses, $K_\perp$ and $K_\parallel$, of this two-compartment system can be related to the system parameters f, $D_a$, $D_e$ and $\lambda$ according to the following exemplary equations:

$$f = \frac{K_\perp}{K_\perp+3}, \quad [109]$$

$$D_e = D_\parallel\left[1+\sqrt{\frac{K_\parallel(1-f)}{3f}}\right], \quad [110]$$

$$D_a = D_\parallel\left[1-\sqrt{\frac{K_\parallel f}{3(1-f)}}\right], \quad [111]$$

$$\lambda = (1-f)\frac{D_e}{D_\perp}. \quad [112]$$

Further Exemplary Methods

A DKI scan was performed on a healthy 28-year-old female volunteer using a 3T Siemens Tim Trio system with a 12-channel head coil. Diffusion-weighted images were acquired along 30 gradient directions with a twice-refocused spin-echo planar imaging (EPI) sequence (TR=5900 ms, TE=96 ms, matrix=82×82, FOV=222×222 mm², 39 slices, slice thickness=2.7 mm, no gap, NEX=11 for b=0, NEX=2 for b=1000, 2000 s/mm², acquisition time=13 min.). DTI and DKI parametric maps were calculated using exemplary computational tools in accordance with the present disclosure called Diffusional Kurtosis Estimator (DKE), which can run in, e.g., MATLAB. The exemplary generated maps for $D_\perp$, $D_\parallel$, $K_\perp$, and $K_\parallel$ together with exemplary Equations [109]-[112] were then used to derive exemplary parametric maps for Da, De, f, and λ.

Further Exemplary Results

FIGS. 21(a)-12(c) illustrate exemplary histograms 2101, 2111, 2112, 2121 for f, $D_a$, $D_e$ and λ, respectively, derived from the WM voxels. WM voxels were defined as having a fractional anisotropy (FA) of at least 0.25. The AWF was on average 0.3±0.05 and the tortuosity λ was on average 2.5±0.7. The average diffusivity of the axons was Da=1.1±0.3 μm²/ms and the EAS diffusivity was $D_e$=2.6±0.7 μm²/ms.

FIGS. 22(a)-22(d) show exemplary parametric coronal images and/or maps 2201, 2211, 2221, 2231 of f, $D_a$, $D_e$ and λ, respectively, for one slice as overlays on the MPRAGE image. For example, FIG. 2(a) is an exemplary illustration 2201 with AWF, FIG. 2(b) is an exemplary illustration 2211 with axonal diffusivity Da, FIG. 2(c) is an exemplary illustration 2221 with the extra-axonal diffusivity De, and FIG. 2(d) is an exemplary illustration 2231 with the tortuosity λ.

A exemplary WM mask (FA>0.25) was applied to the exemplary parametric maps. To correct for subject motion and spatial distortion in the DKI EPI images, the b=0 volume was registered to the subject's skull-stripped MPRAGE using the Automatic Registration Toolbox and the exemplary parametric maps were transformed to the subject's MPRAGE volume according to this registration.

Further Exemplary Discussion

In accordance with certain exemplary embodiments of the present disclosure, the bare diffusivity in the intra-axonal space can be found to be smaller than in the extra-axonal space, and the corresponding mean values for the intra- and extra-axonal bulk diffusivities can be in good agreement with the values used in previously considered models for WM. The exemplary model described herein can provide for quantification of the AWF, which is a measure of the axonal density. The mean AWF of 0.3 obtained using this WM model agrees well with literature values. The tortuosity can depend on, e.g., the water fraction of the EAS and can be high in regions with high axonal and myelin density.

For example, the higher values that can be found in the genu and splenium of the corpus callosum for the axonal water fraction and the tortuosity, as shown in FIGS. 22(a)-22(d), can be explained by the high axonal density and/or the presence of myelin. Using an exemplary embodiment according to the present disclosure for DKI analysis, and more specifically the non-invasive measure of the AWF and the tortuosity, can potentially provide important information for, e.g., assessing neuro-psychiatric and/or neuro-degenerative disorders that can be related to myelin dysfunction, such as Alzheimer's disease and/or multiple sclerosis. Since an exemplary DKI dataset can be acquired within a few minutes using certain exemplary procedures according to the present disclosure, such exemplary procedures and systems can provide for, e.g., an exemplary clinical assessment of white matter tissue properties.

The foregoing merely illustrates the principles of the present disclosure. Various modifications and alterations to the described embodiments will be apparent to those having ordinary skill in art the in view of the teachings herein. It will thus be appreciated that those having ordinary skill in art will be able to devise numerous systems, arrangements, and methods which, although not explicitly shown or described herein, embody the principles of the disclosure and are thus within the spirit and scope of the disclosure. In addition, all publications and references referred to above are incorporated herein by reference in their entireties. It should be understood that the exemplary procedures described herein can be stored on any computer accessible medium, including a hard drive, RAM, ROM, removable disks, CD-ROM, memory sticks, etc., and executed by a processing arrangement which can be a microprocessor, mini, macro, mainframe, etc. In addition, to the extent that the prior art knowledge has not been explicitly incorporated by reference herein above, it is explicitly being incorporated herein in its entirety. All publications referenced above are incorporated herein by reference in their entireties.

What is claimed is:

1. A non-transitory computer-accessible medium for determining an orientation distribution function, the computer-accessible medium including instructions thereon, wherein, when a computing arrangement executes the instructions, the computing arrangement is configured to perform procedures comprising:
   receiving data relating to at least one diffusion weighted image;
   determining a measure of a diffusional kurtosis as a function of the received data using a closed form solution procedure; and
   determining at least one orientation distribution function based on the measure of the diffusional kurtosis.

2. The computer-accessible medium of claim 1, wherein the computing arrangement is further configured to resolve at least one fiber crossing using the at least one orientation distribution function.

3. The computer-accessible medium of claim 2, wherein the at least one fiber crossing is a crossing of at least one of two fibers, three fibers or four fibers.

4. The computer-accessible medium of claim 2, wherein the computing arrangement is further configured to provide a directional color map of the at least one fiber crossing, wherein the directional color map includes fiber direction estimates as a function of the at least one orientation distribution function.

5. The computer-accessible medium of claim 1, wherein the computing arrangement is further configured to perform a fiber tractography based on the at least one orientation distribution function.

6. The computer-accessible medium of claim 5, wherein the computing arrangement is further configured to analyze white matter connectivity patterns based on the at least one orientation distribution function.

7. The computer-accessible medium of claim 5, wherein the computing arrangement is further configured to estimate white matter pathways based on the at least one orientation distribution function.

8. The computer-accessible medium of claim 5, wherein the computing arrangement is further configured to analyze fibers tracts which at least one of cross, kiss, branch, merge or splay, based on the at least one orientation distribution function.

9. The computer-accessible medium of claim 1, wherein the received data includes Gaussian diffusion contributions and substantially excludes non-Gaussian diffusion contributions.

10. The computer-accessible medium of claim 1, wherein the received data includes non-Gaussian diffusion contributions and substantially excludes Gaussian diffusion contributions.

11. The computer-accessible medium of claim 1, wherein the received data includes Gaussian diffusion contributions and non-Gaussian diffusion contributions.

12. The computer-accessible medium of claim 1, wherein the received data is an approximation of an integral of a function that is dependent on diffusion and kurtosis coefficients over a perpendicularly-oriented great circle.

13. A system for determining an orientation distribution function, comprising:
a computer arrangement configured to:
receive data relating to at least one diffusion weighted image;
determine a measure of a diffusional kurtosis as a function of the received data using a closed form solution procedure; and
determine at least one orientation distribution function based on the measure of the diffusional kurtosis.

14. The system of claim 13, wherein the computing arrangement is further configured to resolve at least one fiber crossing using the at least one orientation distribution function.

15. The system of claim 14, wherein the at least one fiber crossing is a crossing of at least one of two fibers, three fibers or four fibers.

16. The system of claim 14, wherein the computing arrangement is further configured to provide a directional color map of the at least one fiber crossing, wherein the directional color map includes fiber direction estimates as a function of the at least one orientation distribution function.

17. The system of claim 13, wherein the computing arrangement is further configured to perform a fiber tractography based on the at least one orientation distribution function.

18. The system of claim 17, wherein the computing arrangement is further configured to analyze white matter connectivity patterns based on the at least one orientation distribution function.

19. The system of claim 17, wherein the computing arrangement is further configured to estimate white matter pathways based on the at least one orientation distribution function.

20. The system of claim 17, wherein the computing arrangement is further configured to analyze fibers tracts which at least one of cross, kiss, branch, merge or splay, based on the at least one orientation distribution function.

21. The system of claim 13, wherein the received data includes Gaussian diffusion contributions and substantially excludes non-Gaussian diffusion contributions.

22. The system of claim 13, wherein the received data includes non-Gaussian diffusion contributions and substantially excludes Gaussian diffusion contributions.

23. The system of claim 13, wherein the received data includes Gaussian diffusion contributions and non-Gaussian diffusion contributions.

24. The system of claim 13, wherein the received data is an approximation of an integral of a function that is dependent on diffusion and kurtosis coefficients over a perpendicularly-oriented great circle.

25. A method for determining an orientation distribution function, comprising:
receiving data relating to at least one diffusion weighted image;
determining a measure of a diffusional kurtosis as a function of the received data using a closed form solution procedure; and
determining at least one orientation distribution function based on the measure of the diffusional kurtosis.

26. The method of claim 25, further comprising resolving at least one fiber crossing using the at least one orientation distribution function.

27. The method of claim 25, further comprising performing a fiber tractography based on the at least one orientation distribution function.

28. The method of claim 27, further comprising analyzing white matter connectivity patterns based on the at least one orientation distribution function.

29. The method of claim 27, further comprising estimating white matter pathways based on the at least one orientation distribution function.

30. The method of claim 27, further comprising analyzing fibers tracts which at least one of cross, kiss, branch, merge or splay, based on the at least one orientation distribution function.

* * * * *